United States Patent [19]

Liao et al.

[11] Patent Number: 5,422,371
[45] Date of Patent: Jun. 6, 1995

[54] METHODS AND COMPOSITIONS FOR INHIBITING 5α-REDUCTASE ACTIVITY

[75] Inventors: Shutsung Liao, Chicago, Ill.; Tehming Liang, Centerville, Ohio

[73] Assignee: Arch Development Corp., Chicago, Ill.

[21] Appl. No.: 904,443

[22] Filed: Jul. 1, 1992

Related U.S. Application Data

[63] Continuation-in-part of Ser. No. 889,589, May 27, 1992, abandoned.

[51] Int. Cl.$^6$ ............................................. A61K 31/20
[52] U.S. Cl. .................................. 514/560; 514/703; 554/224; 568/909.5
[58] Field of Search ............... 554/221, 223, 224, 225; 514/560, 703; 568/909.5

[56] References Cited

U.S. PATENT DOCUMENTS

| | | | |
|---|---|---|---|
| 4,191,759 | 3/1980 | Johnston et al. | 424/242 |
| 4,220,775 | 9/1980 | Rasmusson et al. | 221/18 |
| 4,694,023 | 9/1987 | Loev et al. | 554/224 |
| 4,759,880 | 7/1988 | Nicolaok et al. | 554/221 |
| 5,032,514 | 7/1991 | Anderson et al. | 435/138 |

FOREIGN PATENT DOCUMENTS 0004949 12/1979 European Pat. Off.

OTHER PUBLICATIONS

Dinadiao, May Clin. Proc. 66:1018–1028 (1991).
Downing, et al., J. Am. Acad. Dermo. 14:221–225 (1986).
Ehrmann and Rosenfield, J. Clin. Endocrinol. Metab. 71:1 (1990).
Evans, Science 240:889 (1989).
Fang and Liao, Mol. Pharmacol. 5:428 (1969).
Frost and Gomez, Adv. Biol. Skin. 12:403 (1972).
Gent and Ho, Biochemistry 17:3023 (1978).
Gent, et al., J. Biophys. 33:211 (1981).
George, et al., Endocrinology 119:959 (1989).
Gershon and Parmegiani, J. Med. Chem. 10:186 (1967).
International Search Report, PCT/US93/04090.
Anderson and Liao, Nature 219:277 (1968).
Baba, et al., J. Neurochem. 42:192 (1984).
Beato, Cell 56:335 (1989).
Begin, Proc. Nutrition Soc. 49:261–267 (1990).
Bingham and Shaw, J. Endocr. 57:111 (1973).
Bjorneboe, et al., Brit. J. Dermatol. 118:77–83 (1988).
Blohm et al., Endocrinology 119:959 (1986).
Blohm, et al., Biochem. Biophy. Res. Commun. 95:273 (1989).
Bradnt, et al., J. Steroid Biochem Mol. Biol. 37:575 (1990).
Bruchovsky and Wilson, J. Biol. Chem. 243:2012 (1968).

(List continued on next page.)

Primary Examiner—Mukund J. Shah
Assistant Examiner—P. K. Sripada
Attorney, Agent, or Firm—Arnold White & Durkee

[57] ABSTRACT

Disclosed are a novel class of anti-androgenic compounds including saturated and unsaturated fatty acids, their derivatives, and synthetic analogs, according to the following formula:

$$CH_3-(CH_2)_a-(CR_1R_2CH=CH)_b-(CH_2)_c-COOH,$$

wherein $R_1$ and $R_2$ are each either hydrogen or a halogen; wherein a and c are integers from 0–9; wherein b is an integer from 1–6, provided that $$12 < a+c+(3\times b) \leq 22.$$

Also disclose are methods of synthesis of these compounds, and their use in treating disorders associated with androgenic activities. Also disclosed is the use of known compounds not previously known for their anti-androgenic activity in treating disorders related to androgenic activities.

19 Claims, 15 Drawing Sheets

OTHER PUBLICATIONS

Brooks, et al., Proc. Soc. Esp. Biol. Med. 169:67 (1982).
Brooks, et al., Endocrinology 109:830 (1981).
Brooks, et al., The Prostate 3:35 (1982).
Carter and Coffrey, The Prostate 16:39–48 (1990).
Chang and Liao, J. Steroid Biochem. 27:123 (1987).
Cooke and Robaire, J. Biol. Chem. 260:7489 (1985).
Cusan, et al., J. Am. Acad. Dermatol. 23:462–469 (1990).
Dell and Severson, Biochem. J. 258:171 (1989).
Diani et al., J. Clin Endocr. and Metabl. 74:345 (1992).
Gittes, New England J. Med. 324:236 (1991).
Gormley, et al., J. Clin. Endocrinol. Metab. 70:1136 (1990).
Gorski, et al., Ann. Rev. Physiol. 42:17 (1976).
Halgunset, et al., J. Steroid Biochem. 28:731 (1983).
Hall, New Phytol. 71:855 (1972).
Hamilton, Am. J. Anat. 71:451 (1942).
Hammerstein, et al., J. Steroid Biochem. 19:591 (1983).
Hebborn, et al., Arch Dermatol. 124:387–391 (1988).
Herold and Kinsella, Am. J. Clin. Nutr. 43:566 (1986).
Hiipakka, et al., Endocrine Dependent Tumors, ed. Voight & Knabbe 2:43–61 (1991).
Horrobin, et al., J. Am. Acad. Dermatol. 20:1045–53 (1989).
Horszewicz, et al., Cancer Res. 43:1809 (1983).
Huggins and Hodges, Cancer Res. 1:293 (1940).
Ichihara and Tanaka, Biochem. Biophys. Res. Comm. 149:481 (1981).
Imperato-McGinley, Trend Genet. 2:130 (1986).
Imperato-McGinley, et al., J. Clin. Endocr. Metab. 70:77 (1990).
Isaacs, J. Clin. Endocr. Metab. 56:139 (1983).
Jensen, et al., Proc. Nat'l Acad. Sci. (USA) 59:632 (1968).
Kaighn, et al., Invest. Urol. 17:16 (1979).
Karmali, et al., J. Nat'l Cancer Inst. 73:457 (1984).
Kato, J. Steroid Biochem. 34:219 (1989).
Khan, et al., Febs Letter 292:98 (1991).
Kwok, et al., J. Am. Chem. Soc. 109:3684 (1987).
Lands, Ann. Rev. Biochem. 34:313 (1965).
Liang, et al., Endocrinology 112:1460 (1983).
Liang, et al., Endocrinology 115:2311 (1984).
Liang and Heiss, J. Biol. Chem. 256:7998 (1981).
Liang, et al., J. Steroid Chem. 19:385 (1983).
Liang and Liao, Clin. Research 39:720A (1991).
Liao and Fang, Vitamins and Hormones 27:17 (1974).
Liao, et al., Endocrinology 94:1205 (1974).
Liao, et al., J. Biol. Chem. 248:6154 (1973).
Liao, Int. Rev. Cytology 41:87 (1975).
Liao, et al., J. Steroid Biochem. 34:41–51 (1989).
Mock, et al., J. Pediatrics 106:762 (1985).
Moguilewsky and Bouton, J. Steroid Biochem. 31:699 (1988).
Mooradian et al., Endocrine Rev. 8:1 (1987)
Morello, et al., Invest. Derm. 66:319 (1976).
Morse, et al., Brit. J. Dermatol. (1989) 121:75–90.
Munnich, et al., Lancet 2:1080 (1980).
Nalboone, et al., Lipids 25:301 (1990).
Needleman, et al., Ann. Rev. Biochem. 55:69 (1986).
Newman, Proc. Nat'l Acad. Sci. 87:5543–5547 (1990).
O'Malley, Mol. Endocrinol. 4:363 (1990).
Pattison and Buchanan, Biochem, J. 92:100 (1964).
Phillipson, et al., Eng. J. Med. 312:1210 (1985).
Pochi, Ann. Rev. Med. 41:187 (1990).
Rasmusson, et al., J. Med. Chem. 29:2298 (1986).
Rittmaster, et al., J. Androl. 10:259 (1989).
Rittmaster, et al., J. Clin. Endocr. Metab. 65:188–193 (1987).
Rose and Connolly, The Prostate 18:243–254 (1991).
Sansone and Reisner, J. Invest. Dermatol. 56:366 (1971).
Schafer and Kragballe, Lipids 26:557–560 (1991).
Schweikert and Wilson, Clin. Endocrinol. Metab. 38:811 (1974).
Serafini and Lobo, Fert. Steril. 43:74 (1985).
Siiteri and Wilson, J. Clinical Invest. 49:1737 (1970).
Strauss and Yesalis, Ann. Rev. Med. 42:499 (1991).
Strong, et al., Brit. J. Clin. Prac. Nov./Dec.:444–445 (1985).
Synder, Ann. Rev. Med. 35:207 (1984).
Szepesi, et al., J. Nutr. 119:161 (1989).
Tesoriere et al., J. Neurochem. 51:704 (1988).
Tosaki and Hearse, Basic Res. Cardiol. 83:158 (1988).
Vallette, et al., J. Steroid Biochem. 263:3639 (1988).
Vermeulen et al., The Prostate 14:45 (1989).
Voigt, et al., J. Biol. Chem. 248:4248 (1973).
Wenderoth and George, Endocrinology, 113:569 (1983).
Wilson, Am. J. Med. 68:745 (1980).
Wright, Prostaglandins, Leukotrienes and Essential Fatty Acids 38:229 (1989).
Ziboh and Miller, Ann. Rev. Nutr. 10:433 (1990).
Ziboh, Arch Dermatol. 125:241–245 (1989).
Zuniga, et al., J. Nutr. 119:152 (1989).
Begin, et al., NJCI, 5:1053–1061 (1986).
Anderson, et al., Prostaglandins, Leukotrienes and Essential Fatty Acids, 40:137–141 (1990).
Liang, et al., J. Biol. Chem. 260:4890–4895 (1985).

(A mixture of cis and trans isomers)

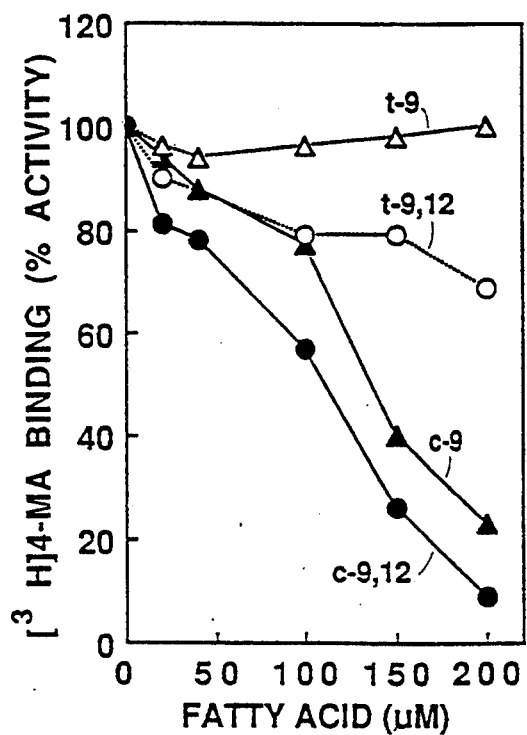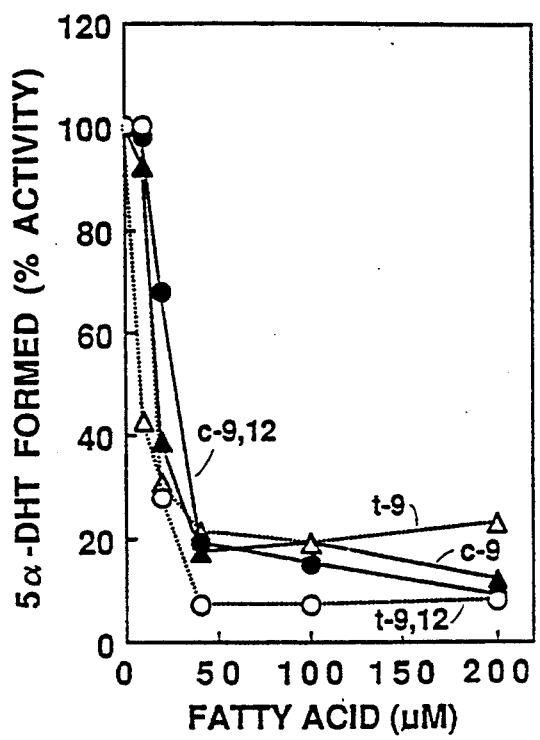
Figure 13 A
Figure 13 B

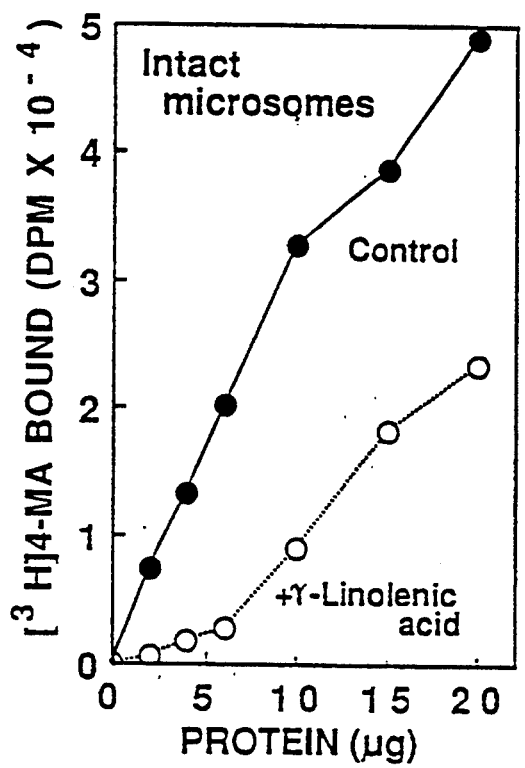
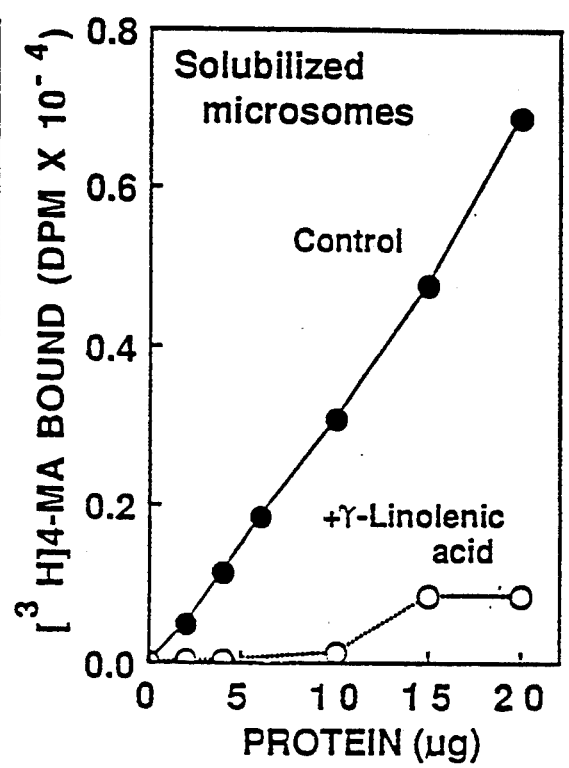
Figure 15 AFigure 15 B

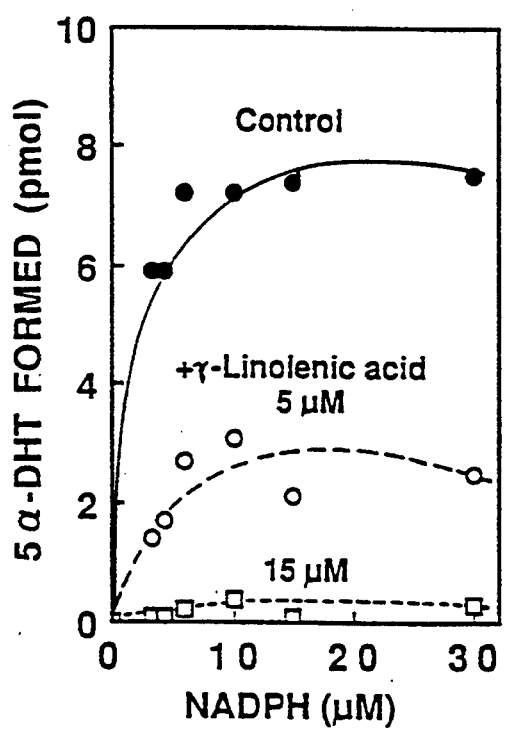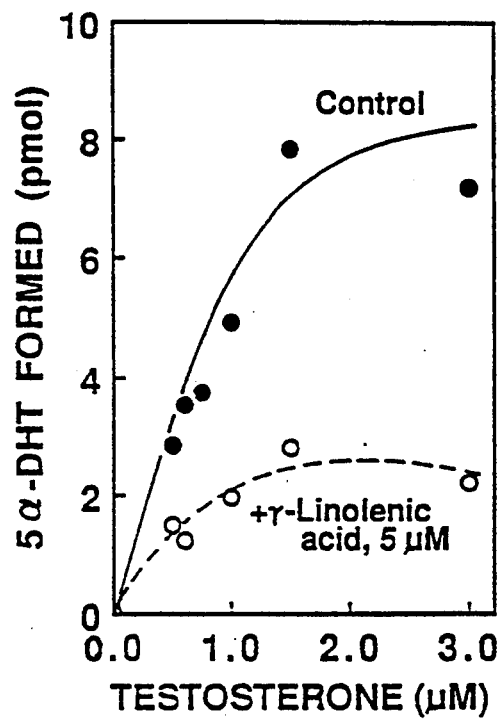
Figure 16 A          Figure 16 B $$CH_3(CH_2)_nCH(F)COOH$$

$$(n=0\sim17)$$

$$F(CH_2)_nCOOH$$

$$(n=1\sim19)$$

$$FCH_2(CH_2)_{7-n}CH=CH(CH_2)_{7+n}COOH$$

$$(n=0\sim7)$$

$$F(CH_2)_nCH(R)(CH_2)_mCOOH$$

$$(n=5\sim8; m=0\sim8; R=CH_3, C_2H_5, C_3H_7)$$

$$CF_3(CH_2)_{14}CF_2CF_2COOH$$

$$CH_3(CH_2)_{13-m}CF_2(CH2)_{m-2}COOH$$

$$(m=0\sim13)$$

Figure 18

METHODS AND COMPOSITIONS FOR INHIBITING 5α-REDUCTASE ACTIVITY

CROSS-REFERENCED AND RELATED APPLICATION

This application is a continuation-in-part application of U.S. patent application Ser. No. 07/889,589, filed May 27, 1992, now abandoned, the disclosure of which is incorporated herein by reference.

BACKGROUND OF THE INVENTION
1. Field of the Invention

The present invention relates generally to compounds, compositions and methods regulating the actions of androgens and other steroid hormones by modulating the activity of 5α-reductase. More particularly, the present invention relates to the use of these compounds to treat disorders that are caused by excess androgen action in cells or organs.
2. Description Of The Related Art
A. Steroid Hormones and Their Receptors Androgens are one of the six major classes of steroid hormones. Steroid hormones form complexes with specific receptor proteins in selective cells of target organs [Jensen et al., *Proc. Nat'l Acad. Sci.*(USA), 59:632 (1968); Liao, *Intl. Rev. Cytology* 41:87 (1975); Gorski, et at., *Ann. Rev. Physiol.* 42:17 (1976)]. Steroid receptors are members of a superfamily of transcription factors that can regulate gene expression, and this function is dependent on the binding of a specific hormonal ligand to an appropriate receptor [Evans, *Science* 240:889 (1989); Beato, *Cell* 56:335 (1989); O'Malley, *Mol. Endocrinol.* 4:363 (1990)].

Studies of the specificity and affinity of steroid hormones for their receptors have contributed greatly to the understanding of the relationships among steroid and receptor structures and biological activity, target organ specificity, and the mechanism of action of many antihormones, including "competitive antiandrogens". "Competitive Antiandrogens" are defined herein as those antiandrogens that interact with receptors and competitively prevent receptor binding of active androgens [Fang and Liao, *Mol. Pharmacol.* 5:428 (1969); Liao et al., *J. Biol. Chem.* 248:6154 (1973); Liao et al., *Endocrinology* 94:1205 (1974); Chang and Liao, *J. Steroid Biochem.* 27:123 (1987); Liao et al., *J. Steroid Biochem.* 34:41 (1989)], although it should be noted that some compounds with an antiandrogenic activity may act by a different mechanism.

B. Androgen Actions

Androgen, produced in the testis, stimulates the differentiation of the male reproductive organs, including the penis, scrotum, prostate, seminal vesicles, epididymis, and vas deferens. With the onset of puberty, an increase in the production of androgen promotes the growth of these tissues. Androgen is required for spermatogenesis and accelerates skeletal muscular growth and bone formation. In the central nervous system, it stimulates libido and produces feedback inhibition of gonadotropin secretion. In skin, androgen increases the size of sebaceous glands and apocrine glands and converts villus hairs in the axillae, pubic region, and the beard to form coarser and longer terminal hairs. Androgen causes thickened vocal cords and lowers the pitch of the voice. Androgen also stimulates hematopoiesis. Uses of androgen known to the medical arts include, for example, treatment of hypogonadism and anemia [Synder, *Ann. Rev. Med.* 35:207 (1984); Mooradian et at., *Endocrine Rev.* 8:1 (1987)]. The abuse of androgen among athletes to enhance performance is well known [Strauss and Yesalis, Annu. *Rev. Med.* 42:499 (1991)].

Androgen is also known to promote the development of benign prostatic hyperplasia (BPH) [Wilson, *Am. J. Med.* 68:745 (1980)], prostate cancer [Huggins and Hodges, *Cancer Res.* 1:293 (1940)], baldness [Hamilton, *Am. J. Anat.* 71:451(1942)], acne [Pochi, *Annu. Rev. Med.* 41:187 (1990)], hirsutism, and seborrhea [Hammerstein et at., *J. Steroid Biochem.* 19:591 (1983); Moguilewsky and Bouton, *J. Steroid Biochem.* 31:699 (1988)]. Approximately 70% of males in the United States over the age of 50 have pathological evidence of BPH [Carter and Coffey, *The Prostate* 16:39–48 (1990)]. Prostate cancer is the second leading cause of cancer death in males in the United States [Silverberg and Lubera, *Cancer Statistics,* 40:9 (1990); Gittes, *New England J. Medicine* 324:236 (1991)]. Male-patterned baldness can start as early as the teens in genetically susceptible males, and it has been estimated to be present in 30% of Caucasian males at age 30, 40% of Caucasian males at age 40, and 50% of Caucasian males at age 50. Acne is the most common skin disorder treated by physicians [Pochi, *Ann. Rev. Med.* 41:187 (1990)] and affects at least 85% of teenagers. In women, hirsutism is one of the hallmarks of excessive androgen action [Ehrmann and Rosenfield, *J. Clin. Endoerinol. Metab.* 71:1 (1990)]. The ovaries and the adrenals are the major sources of androgen in women.

Differential Actions of Testosterone and 5α-Dihydrotestosterone (DHT)

In men, the major androgen circulating in the blood is testosterone. About 98% of the testosterone in blood is bound to serum proteins (high affinity binding to sex-steroid binding globulin and low affinity binding to albumin), with only 1–2% in free form [Liao and Fang, *Vitamins and Hormones* 27:17 (1969)]. The albumin bound testosterone, the binding of which is readily reversible, and the free form are considered to be bioavailable, and account for about 50% of total testosterone. Testosterone enters target cells, apparently by diffusion. In the prostate, seminal vesicles, skin, and some other target organs it is converted by a NADPH-dependent 5α-reductase to a more active metabolite, DHT. DHT then binds to androgen receptor (AR) in target organs [Anderson and Liao, *Nature* 219:277 (1968); Bruchovsky and Wilson, *J. Biol. Chem.* 243:2012 (1968); Liao, *Int. Rev. Cytology* 41:87 (1975)]. The DHT-receptor complexes interact with specific portions of the genome to regulate gene activities [Liao et al., *J. Steroid Biochem.* 34:41 (1989)]. Testosterone appears to bind to the same AR, but it has a lower affinity than DHT. In tissues such as muscle and testes, where 5α-reductase activity is low, testosterone may be the more active androgen.

The difference between testosterone and DHT activity in different androgen-responsive tissues is further suggested by findings in patients with 5α-reductase deficiency. Males with 5α-reductase deficiency are born with female-like external genitalia. When they reached puberty, their plasma levels of testosterone are normal or slightly elevated. Their muscle growth accelerates, the penis enlarges, voice deepens, and libido toward females develops. However, their prostates remain nonpalpable, they have reduced body hair, and they do not develop acne or baldness. Females with 5α-reductase deficiency do not have clinical symptoms [Imperato-McGinley, *Trend Genet* 2:130 (1986)].

The findings in 5α-reductase deficient patients suggest that inhibitors of 5α-reductase would be useful for the treatment of prostatic cancer, BPH, acne, baldness, and female hirsutism. Clinical observations and animal experiments have indicated that spermatogenesis, maintenance of libido, sexual behavior, and feed-back inhibition of gonadotropin secretion do not require the conversion of testosterone to DHT [Brooks et al., *Proc. Soc. Exp. Biol. Med.* 169:67 (1982); Blohm et at., *Endocrinology* 119:959 (1986); George et at., *Endocrinology* 119:959 (1989)]. This is in contrast to other hormonal therapies which abolish the actions of both testosterone and DHT.

Treatments of androgen-dependent skin and prostatic diseases by 5α-reductase inhibitors would be expected to produce fewer side effects than the presently available hormonal therapies. These include castration, estrogen therapy, high doses of superactive gonadotropin-releasing hormone such as Luprolide, and the use of competitive antiandrogens which inhibit AR binding of testosterone and DHT, such as flutamide, cyproterone acetate and spironolactone. The long term efficacy of 'competitive antiandrogens' is also compromised by their block of the androgenic feedback inhibition of gonadotropin secretion. This results in elevated gonadotropin secretion, which in turn increases testicular secretion of testosterone. The higher level of testosterone eventually overcomes the action of the antiandrogen.

D. Biological Importance of 5α-Reductase

Excessive DHT is implicated in certain androgen-dependent pathological conditions including BPH, ache, male-pattern baldness, and female idiopathic hirsutism. It has been shown that 5α-reductase activity and the DHT level are higher in the presence of BPH prostates than that of the patients with normal prostates [Isaacs, *J. Clin. Endocrinol. Metab.* 56:139 (1983); Siiteri and Wilson, *J. Clinical Invest.* 49:1737 (1970)]. 5α-Reductase activity is reported to be higher in hair follicles from the scalp of balding men than that of nonbalding men [Schweikert and wilson, *Clin. Endocrinol. Metab.* 38:811 (1974)].

In a given individual, 5α-reductase activity is found to be higher in balding skin than from hairy skin [Bingham and Shaw *J. Endocr.* 57:111 (1973)]. Some idiopathic hirsute women have a normal circulating level of testosterone, but their affected skin has a higher 5α-reductase activity than that of nonhirsute women [Serafini and Lobo, *Fert Steril* 43:74 (1985)]. An increased 5α-reductase activity has also been reported for skin with acne [Sansone and Reisner, *J. Invest. Dermat.* 56:366 (1971)].

Genetic evidence also supports the suggestion that DHT plays an important role in the development of BPH and the above skin conditions. In males with hereditary 5α-reductase deficiency, their prostates remain small or nonpalpable after puberty. They do not develop acne, temporal hairline recession, or baldness. Compared to their fathers and brothers, they have scanty beards and reduced body hair.

E. Steroidal 5α-Reductase Inhibitors

The most potent inhibitors of 5α-reductase developed so far are steroids or their derivatives. Among these the 4-azasteroidal compounds (Merck Co.) are the most extensively studied [Liang et al., *J. Steroid Chem.* 19:385 (1983); Rasmusson et al., *J. Med. Chem.* 29:2298 (1986)].

These inhibitors are 3-oxo-4-aza-5α-steroids with a bulky functional group at the 17β-position, and act by reversibly competing with testosterone for the binding site on the enzyme.

The A-ring conformation of these compounds is thought to be similar to the presumed 3-enol transition state of the 5α-reduction of 3-oxo-$\Delta^4$-steroids. A prototype for 5α-reductase inhibitors is 17β-N,N-diethylcarbamoyl-4-methyl-4-aza-5α-androstan-3-one (4-MA), which behaves as an inhibitor of 5α-reductase in vivo, decreasing the prostatic concentration of DHT in intact male rats or in castrated male rats given testosterone propionate. 4-MA attenuated the growth of the prostate of castrated rats induced by testosterone, but had much less of an effect in rats given DHT [Brooks et al., *Endocrinology* 109:830 (1981)].

When dogs are treated with 4-MA, the prostate size decreases [Brooks et al., *The Prostate* 3:35 (1982); Wenderoth and George, *Endocrinology*, 113:569 (1983)]. Topical applications of 4-MA to the scalp of the stumptail macaque, a primate model of human male pattern baldness, also prevented the baldness which normally occurs at puberty in these monkeys [Rittmaster et al., *J. Clin Endocrinol. Metab.* 65:188 (1987)]. These results also suggest that the growth of the prostate in rats and dogs, and baldness in the stumptail macaque depend on DHT.

On the other hand, studies in rat pituitary cultures showed that complete inhibition of testosterone conversion to DHT by 4-MA did not affect testosterone inhibition of LH release, indicating direct action of testosterone in this system [Liang et al., *Endocrinology* 115:2311 (1984)].

Another potent inhibitor is Proscar (Merck Co.) (finasteride, MK-906, or 17β-N-t-butylcarbamoyl-4-aza-5α-androst-1-en-3-one). The inhibitor has no significant affinity for the rat prostate AR. In clinical trials, Proscar decreases the plasma level of DHT and the size of the prostate and also improves urinary flow in patients with benign prostatic hyperplasia [Vermeulen et al., *The Prostate* 14:45 (1989); Rittmaster et al., *J. Androl.* 10:259 (1989); Gormley et at., *J. Clin. Endocrinol. Metab.* 70:1136 (1990); Imperato-McGinley et at., *J. Clin. Endocrinol. Metab.* 70:777 (1990)]. In stumptail macaque monkeys, Proscar administered orally at 0.5 mg/day, alone or in combination with topical 2% minoxidil, reduced serum DHT level, and reversed the balding process by enhancing hair regrowth by topical minoxidil [Diani et at., *J. Clin. Endocr. and Metab.* 74:345 (1992)]. The effects of Minoxidil and Proscar were additive.

Among other steroidal compounds shown to inhibit 5α-reductase are 4-androstane-3-one-17β-carboxylic acid [Voigt et al., *J. Biol. Chem.* 260:4890 (1985)] and 4-diazo-21-hydroxymethyl-pregnane-3-one [Blohm et at., *Biochem. Biophy. Res. Commun.* 95:273 (1989)], and 3-carboxy A-ring aryl steroids [Brandt et at., *J. Steroid Biochem. Mol. Biol.* 37:575 (1990)].

F. Biological Effects of Fatty Acids and Lipids

Since treatments of androgen-dependent skin and prostatic diseases by 5α-reductase inhibitors can produce fewer side effects than the hormonal therapies which indiscriminately inhibit all androgen actions, it is desirable to provide different types of 5α-reductase inhibitors. This invention deals with the use of natural and synthetic fatty acids, especially polyunsaturated fatty acids and their derivatives as 5α-reductase inhibitors for therapeutic agents.

It is known that polyunsaturated fatty acids can correct the effects of fatty acid deficiencies that manifest as dermatitis, kidney necrosis, infertility, and cardiovascular diseases [Herold and Kinsella, *Am. J. Clin. Nutr.* 43:566 (1986); Phillipson et at., *Eng. J. Med.* 312:1210 (1985); Ziboh and Miller, *Annu. Rev. Nutr.* 10:433 (1990)] and also can exhibit anti-tumor activities [Begin, *Proc. Nutrition Soc.* 49:261 (1990); Karmali et at., *J. Natl. Cancer Inst.* 73:457 (1984)]. Many unsaturated fatty acids are essential components of mammalian membranes, typically in the acylated form of triglycerides and phospholipids [Lands, *Ann. Rev. Biochem.* 34:313 (1965)].

Arachidonic acid serves as a specific precursor in the biosynthesis of prostaglandins and leukotrienes [Needleman et at., *Ann. Rev. Biochem.* 55:69 (1986)]. These metabolites of unsaturated fatty acids are mediators of inflammation. Unsaturated essential fatty acids have been implicated as dietary factors that influence acne. However, no firm support for this view has developed, and no successful treatment based on this idea has appeared [Downing et at., *J. Am. Acad. Dermatology* 14:221 (1986)]. Synthetic retinoids and AR binding competitive antiandrogens have been used to obtain therapeutic improvement of acne in some individuals. These anti-acne agents increase the proportion of linoleic acid in sebum in parallel with clinical improvement [Wright, *Prostaglandins, Leukotrienes and Essential Fatty Acids* 38:229 (1989)].

G. Biochemical Effects of Fatty Acids and Lipids

Several membrane-associated enzymes (e.g., 5'-nucleotidase, acetyl CoA carboxylase) have been shown to be affected by the polyunsaturated fatty acid content of dietary fat, and to alter the physicochemical properties of cellular membranes [Zuniga et al., *J. Nutr.* 119:152 (1989); Szepsesi et at., *J. Nutr.* 119:161 (1989)]. Various types of phospholipases in rat ventricular myocytes are modulated differentially by different unsaturated fatty acids in the culture media [Nalboone et at., *Lipids* 25:301 (1990)]. In addition, treatment of cerebral cortical slices [Baba et at., *J. Neurochem.* 42:192 (1984)] or intact retina [Tesoriere et al., *J. Neurochem.* 51:704 (1988)] with unsaturated fatty acids can enhance adenyl cyclase activities.

Very few studies, however, have been directed to the elucidation of the mode of action of free fatty acids on enzymes in cell-free systems. Certain cis-unsaturated fatty acids, at 50 $\mu$M, were shown to stimulate protein kinase C activity [Dell and Severson, *Biochem. J.* 258:171 (1989); Khan et at., *Febs Letter* 292:98 (1991)] and to inhibit steroid binding to receptors for androgens, estrogens, glucocorticoids, and progestins [Vallette et at., *J. Steroid Biochem.* 263:3639 (1988); Kato, *J. Steroid Biochem.* 34:219 (1989)]. No evidence has been presented to show that unsaturated fatty acids can affect steroid receptor binding of steroid hormones in vivo in an animal or human.

Fatty acids fluorinated at $\alpha$, $\beta$, and $\omega$ positions [Gershan and Parmegiani, *J. Med. Chem.* 10:186 (1967); Pattison and Buchanan, *Biochem. J.* 92:100 (1964); Gent and Ho, *Biochemistry* 17:3023 (1978)] and $\omega$-oleic acids [Tosaki and Hearse, *Basic Res. Cardiol.* 83:158 (1988)] have been identified in plants and microorganisms, and have been chemically synthesized. Many of these fluorinated acids are toxic. Degradation of some fluorinated fatty acids can yield fluoro-acetic acid, which can be incorporated into fluorocitrate and can then block aconitase action. This can cause inhibition of the citric acid cycle and cellular energy production [Hail, *New Phytol.* 71:855 (1972)]. Fluorinated fatty acids are often useful in the studies of fatty acid degradation, metabolism and transport in biological systems [Stoll et al., *J. Lipid Res.* 32:843 (1991)], and biophysical studies of protein-lipid interaction and membranes functions [Gent et al., *Biophys. J.* 33:211 (1981)].

Biotin is a cofactor of major carboxylases which are necessary for orderly production and metabolism of fatty acids. Alopecia caused by biotin-deficiency can be completely treated by biotin administration to patients. Oral administration and cutaneous application of unsaturated fatty acids can also improve biotin-dependent dermatological conditions including scalp hair growth [Munnich et al., *Lancet* 2:1080 (1980); Mock et al., *J. Pediatrics* 106:762 (1985)]. The fatty acid effect is apparently due to supplementation of the deficient fatty acids and not related to regulation of androgen action involved in male pattern-alopecia.

SUMMARY OF THE INVENTION

The present invention relates generally to the utilization of fatty acids and their derivatives for the control of androgen activity in target organs and cells through the modulation of 5$\alpha$-reductase activity. The present invention deals with the utilization of new or known fatty acids and related compounds to repress androgenic activity by inhibiting the formation and availability of active androgen in target cells. The invention is useful for the treatment of prostatic hyperplasia, prostatic cancer, hirsutism, acne, male pattern baldness, seborrhea, and other diseases related to androgen hyperactivity.

The compounds of the present invention include various isomers of saturated and unsaturated fatty acids, natural and synthetic analogs, and derivatives from which these fatty acids can be generated as well as the metabolites and oxidation products of these fatty acids. These fatty acids can affect the transformation of androgens by inhibition of 5$\alpha$-reductase, and as a result can (a) limit the supply of DHT to target organs and suppress the DHT-dependent androgen actions, or (b) prevent the metabolic loss of testosterone or other androgenic precursors of DHT and promote or maintain hormone actions that are dependent on testosterone or other precursors of DHT.

Since 5$\alpha$-reductase can also use other steroids as substrates, these compounds can also regulate the transformation and activation of other 3-oxo-$\Delta^4$-steroids and, therefore, can control the biological functions of other steroid hormones through the same mechanism. The synthetic fatty acid analogs of the present invention are unique in that they are relatively stable in vivo and in vitro and are not easily metabolized, degraded, or incorporated into lipid structures or other derivatives. This stability is conferred by fluorination, alkylation, and cyclization of fatty acids. The synthetic compounds are expected to have desired effectiveness and organ specificity for use as therapeutic agents without significant side effects.

The use of the effective compounds known previously or newly disclosed in the present invention, in therapeutically effective amounts of pharmaceutical compositions containing one or more of the compounds of the invention, in some cases in combination with other therapeutic agents and carriers, or in natural or synthetic products, is appropriate in the treatment of various disorders. These disorders include those conditions wherein excessive androgenic activities have been implicated, including, for example, male pattern baldness, female hirsutism, acne, BPH, and prostate cancer.

These pharmaceutical compositions, comprising known fatty acids or compounds of the invention, can be administered by topical or internal routes, including oral, injection, or other means, such as topical creams, lotions, hair tonics, scalp care products, or transdermic patch applications, alone or in combination with other drugs, drug additives, or pharmaceutical compounds. It is also expected that some of these compounds may act to regulate steroid metabolism, and may thereby affect the function of normal or mutated hormone receptors. Therefore, these compositions may be useful in the treatment of androgen and other hormone-sensitive or insensitive disorders or tumors. It is also expected that compounds of the invention will be important in the studies of the mechanism of action of hormones and anti-hormones.

BRIEF DESCRIPTION OF THE DRAWINGS

FIG. 13 shows the effects of oleic acid (C18:1,cis-9) (c-9), linoleic acid (C18:2,cis-9,12) (c-9,12), elaidic acid (C18:1,trans-9) (t-9), and linolelaidic acid (C18:2,trans-9,12) (t-9,12) on rat liver microsomal 5α-reductase activity as determined by [$^3$H]4-MA binding assay (left) or the enzymatic assay (fight). The abbreviations in parentheses indicate: the number of carbon atoms in the carbon chain, the number and the position of cis or trans double bonds and abbreviation shown in the figures. The amount of rat liver microsomes was 10 μg protein in the binding assay and 2 μg protein in the enzymatic assay. In the absence of lipid, the control value for the [$^3$H]4-MA binding assay was 30618±975 dpm. The control value for the enzymatic assay was 9.0±0.9 nmol 5α-DHT formed/15 min using 0.5 μM testosterone as substrate. These control values were taken as 100% activity.

FIG. 15 shows the inhibition of [$^3$H]4-MA binding to 5α-reductase in the intact (left figure) and detergent solubilized (right figure) rat liver microsomes by γ-linolenic acid. The [$^3$H]4-MA-binding assay was carried out in the absence (control) and presence of 10 μM of γ-linolenic acid and varying mounts of microsomal protein.

FIG. 16 shows the inhibition of 5α-reductase activity by γ-linolenic acid at varying concentrations of NADPH (left) and testosterone (right). The concentrations of γ-linolenic acid are shown in the figures.

FIG. 18 shows fatty acids described by others previously, which can be used to regulate 5α-reductase activity.

DETAILED DESCRIPTION OF THE PREFERRED EMBODIMENTS

The following examples illustrate the rationale and practice of the inventions. Although many of the examples are base, on the actions of androgens and androgen receptors (ARs), they may also apply to the function of other steroid hormones which is dependent on or regulated by 5α-reductase.

EXAMPLE 1

Synthesis of Fatty Acid Analogs and Related Molecules

A. Synthesis of Beta-fluoro Fatty Acids

Figure 1:
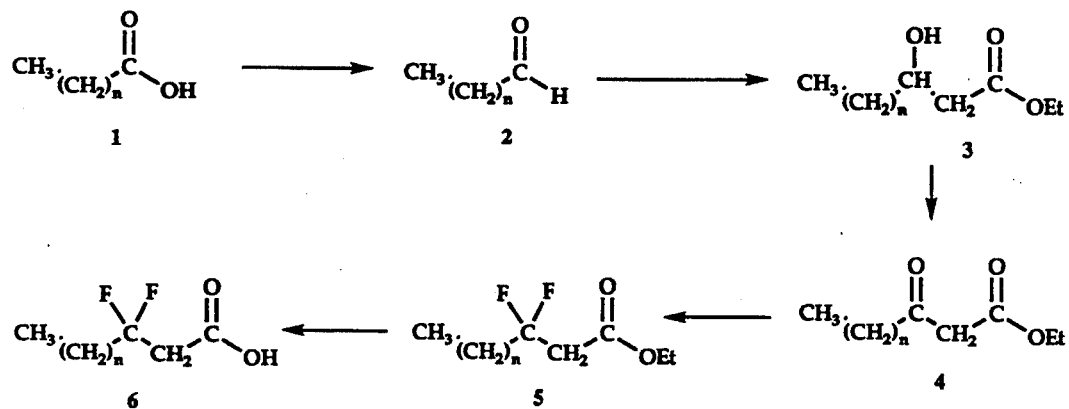
FIG. 1 is a schematic representation of the synthesis of compounds 2 to 6 of Example 1.

The synthesis of β-fluoro acid analogs of linolenic acid is a relatively straightforward process. Starting with the appropriate 16-carbon acid 1 (FIG. 1), aldehyde 2 can be obtained through reduction using isopentyl boron hydride. β-Hydroxy acetate 3 can be made from 2 using zinc and ethyl bromoacetate in a Reformatski-type reaction. The β-keto ester 4 can be made from 3 using pyridinium dichromate in dichloromethane at room temperature. The difluoro ester 5 can be made from 4 using diethylaminosulfer trifluoride (DAST) in methylene chloride at room temperature. DAST is a fluorination reagent which is very selective for aldehydes, ketones and alcohols at room temperature. The free acid 6 is obtained via base hydrolysis of the ester group.

Figure 2:
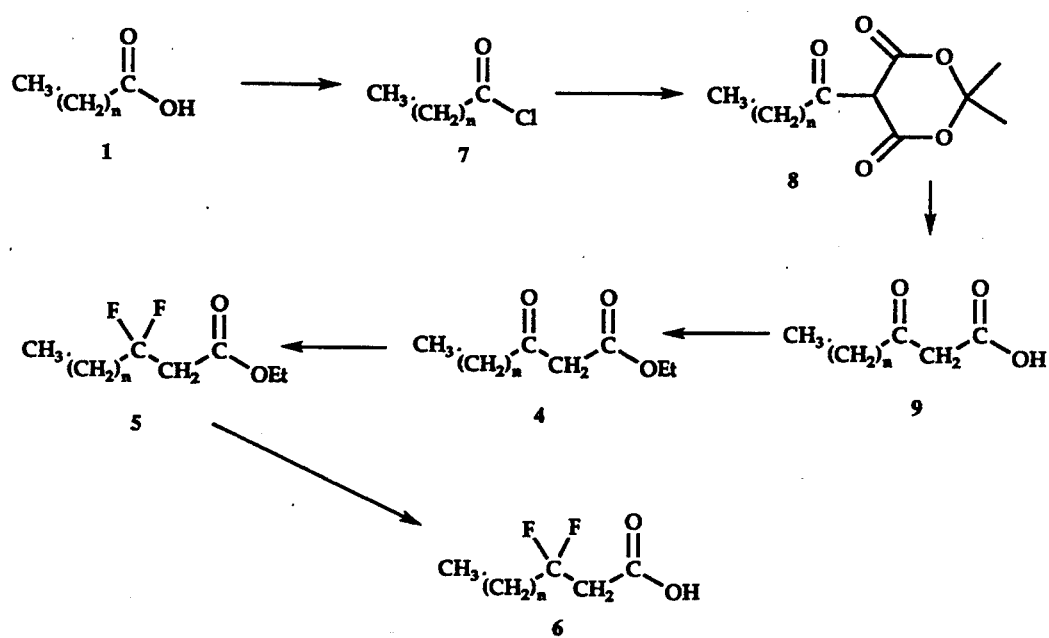
FIG. 2 is a schematic representation of the synthesis of compounds 4 to 9 of Example 1.

Alternatively, one could produce the acid chloride 7 from 1 by reaction with thionyl chloride (FIG. 2). Compound 8 can be made by reaction of 7 with Meldrum's acid, which is the product from the reaction of malonic acid with acetone. Compound 8 undergoes ring opening and decarboxylation to form β-keto acid 9. From the β-keto acid 9 the sequence continues to produce compounds 4, 5, and the target compound 6 as previously described above.

B. Synthesis of 6-Membered Ring Linolenic Acid Mimetics

Figure 3:
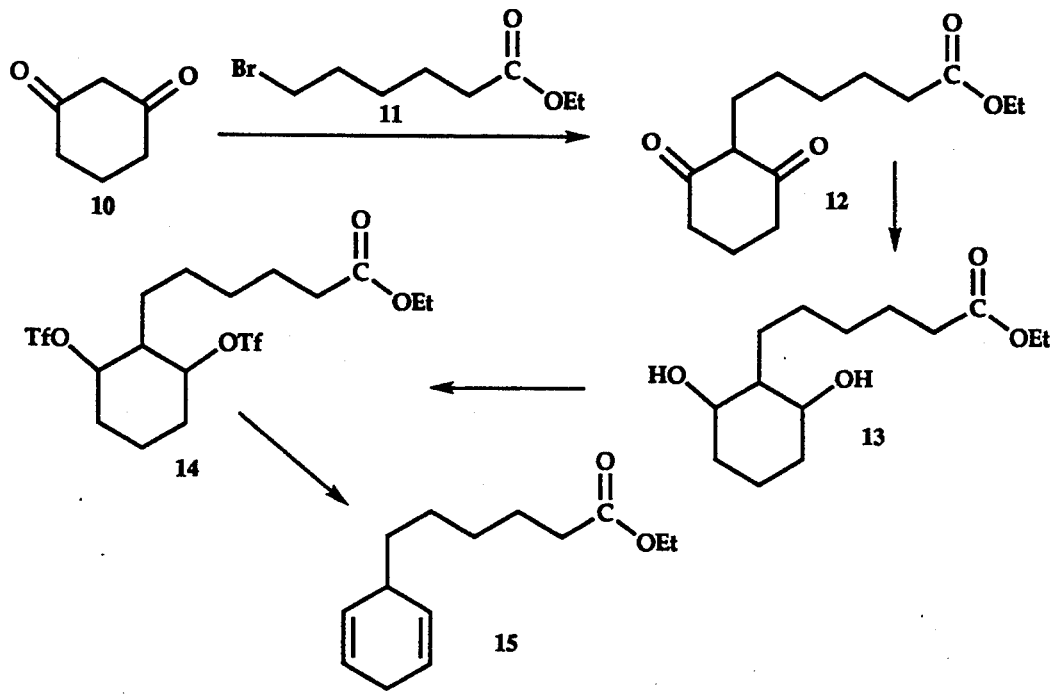
FIG. 3 is a schematic representation of the synthesis of compounds 12 to 15 of Example 1.

Since the two key groups present in linolenic acid are 1) three cis double bonds and 2) the carboxylic acid group, a molecule can be designed that possess the same key groups and retains the activity of linolenic acid. Examples of such compounds are 15 and 21, the synthetic routes to which are shown in FIGS. 3 and 4.

Starting from 1,3-hexanedione 10 one can produce compound 12 by forming the enolate anion of 10 followed by reaction with ethyl 6-bromocaproate 11. Reduction using sodium borohydride then gives compound 13. Reaction of 13 with trifluoromethylsulfonic anhydride gives the ditrifluoromethylsufonate (ditriflate) 14. Compound 14 can be transformed into the target linolenic acid mimic 15 by double elimination of triflate using 1,5-diazabicyclo[5.4.0]undec-5-ene (DBU). The free acid can be obtained or it can be formed in vivo by enzymatic hydrolysis of the ester group.

Figure 4:
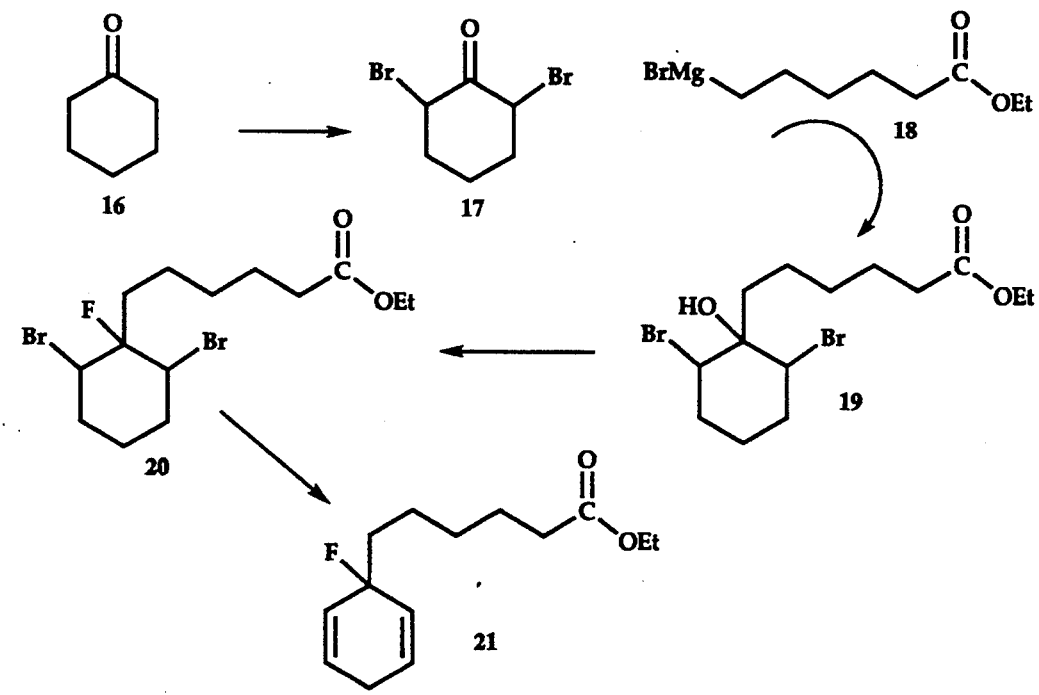
FIG. 4 is a schematic representation of the synthesis of compounds 17, and 19 to 21 of Example 1.

Another linolenic acid mimetic is compound 21, the synthesis of which is shown in FIG. 4. Starting from cyclohexanone 16, one can obtain the dibromoketone 17 through reaction with pyridinium bromide perbromide. Reaction of 17 with the Grignard reagent 18 gives the dibromohydroxyl ester 19. Fluorination of 19 at room temperature using DAST gives compound 20, which when stirred with DBU at room temperature undergoes double elimination of HBr to give the target linolenic acid mimetic 21. Again the free acid can be obtained by chemically removing the ester function or by enzymatic hydrolysis in vivo.

C. Synthesis of C17-Ring Linolenic Acid Analogs

Figure 5:
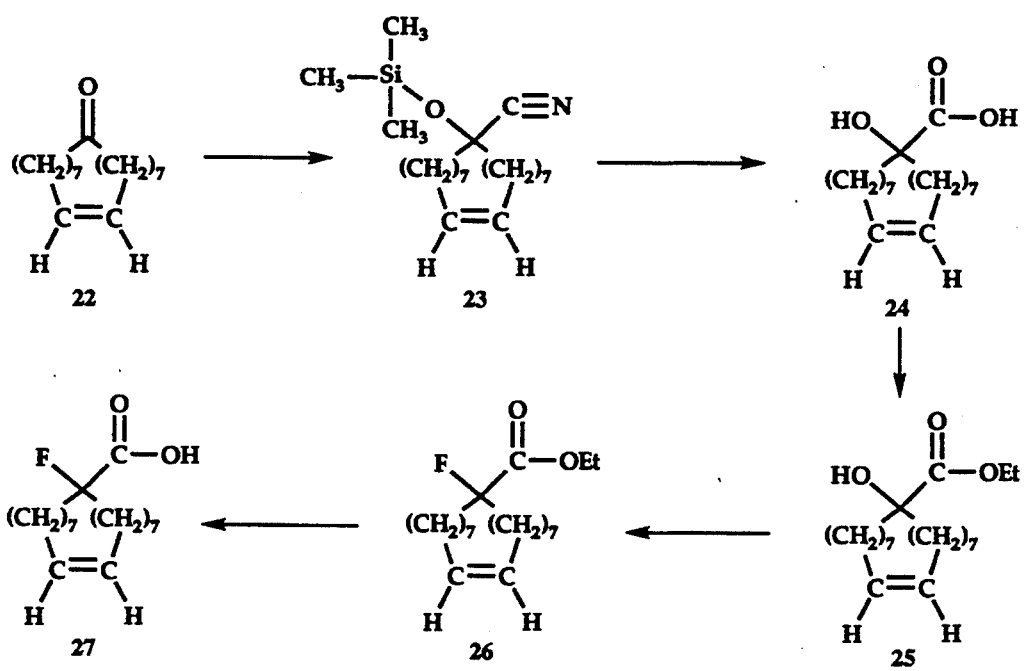
FIG. 5 is a schematic representation of the synthesis of compounds 23 to 27 of Example 1.

Cyclic analogs of linolenic acid should be more stable in vivo than linolenic acid itself, due to greater resistance to β-oxidative cleavage. An example of one class of cyclic compounds is compound 27, which is a 17-membered hydrocarbon ring possessing a double bond and the required carboxylic acid group. The synthetic route to compound 27 is depicted in FIG. 5. Starting from civetone 22, the silated cyanohydrin 23 can be formed by reaction with trimethylsilyl cyanide. The cyanohydrin can be converted to the α-hydroxy acid 24 via reduction with stannous chloride and hydrochloric acid. Esterification of 24 gives compound 25, which can be converted to the α-fluoro ester 26 through reaction with DAST. Cleavage of the ester group then gives the free acid 27.

Figure 6:
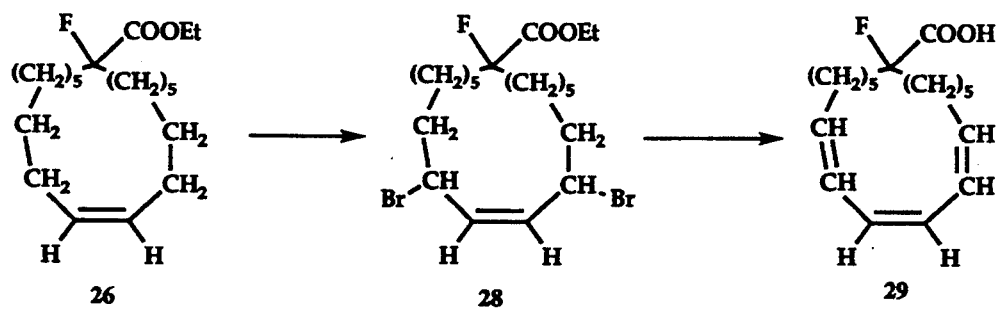
FIG. 6 is a schematic representation of the synthesis of compounds 28 and 29 of Example 1.

Fluoro ester 26 can also undergo allelic bromination to give compound 28 (FIG. 6), which undergoes double elimination by reaction with DBU to give the tri-ene 29, most likely as a mixture of cis and trans isomers. Fluoro ester 26 can also be catalytically hydrogenated to give the C17-saturated ring compound as well (not depicted).

Figure 7:
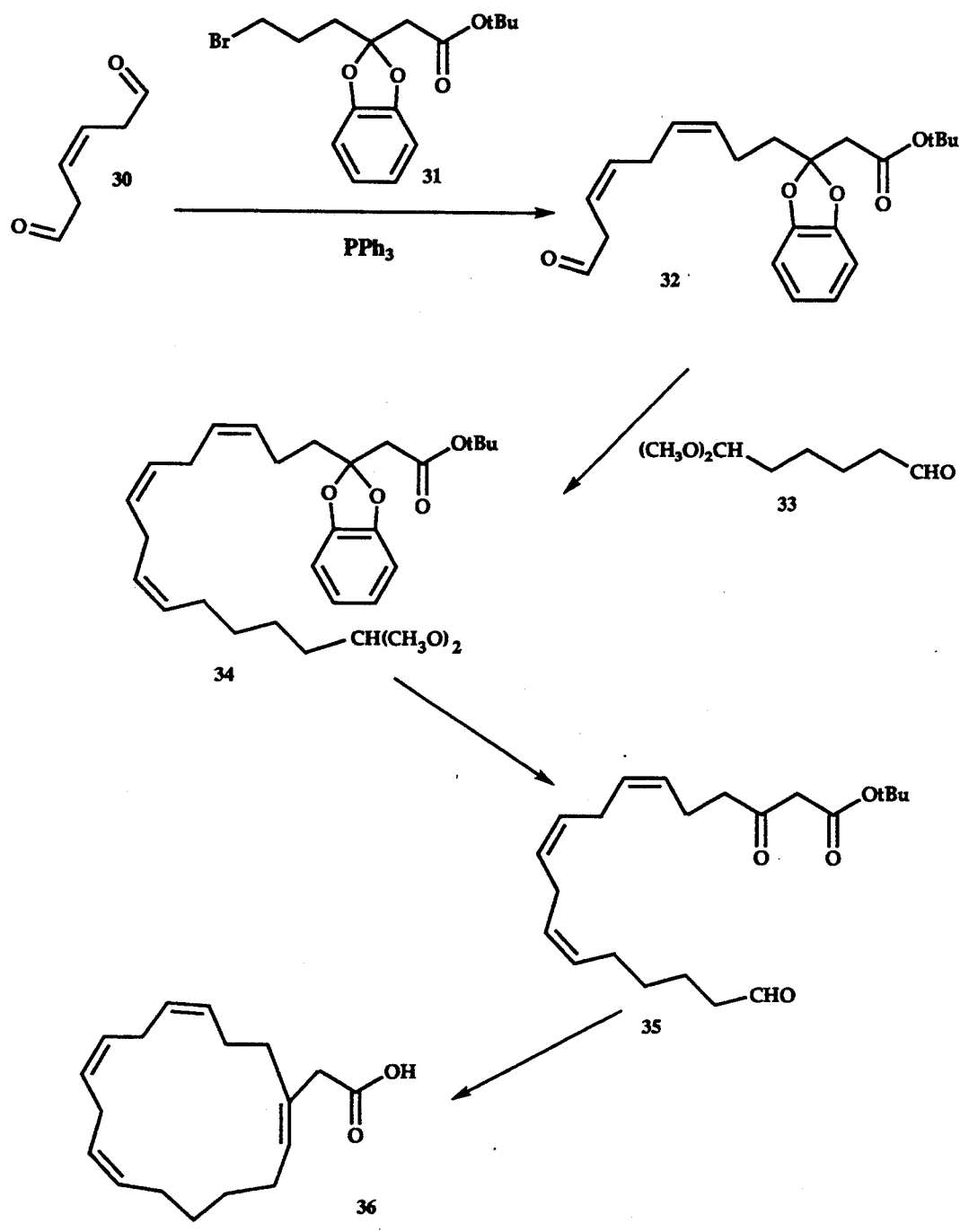
FIG. 7 is a schematic representation of the synthesis of compounds 32 and 34 to 36 of Example 1.

D. Synthesis of C16-Ring and 16-Membered Hetero Atom-substituted Ring Linolenic Acid Analogs The synthesis of this class of compounds begins with 3-hexenedial 30 (FIG. 7). Reaction of 30 with compound 31 (prepared in six steps from butyrolactone) and triphenylphosphine gives the Wittig product 32. Reaction of 32 with aldehyde 33 (prepared in four steps from cyclohexene) gives compound 34, which leads to compound 35 after removal of the ketal protecting groups. Compound 36 is obtained from the carbonyl coupling of 35 via titanium (III) chloride and lithium in dry dimethyoxyethane.

Insertion of heteroatoms into the ring system is accomplished by the procedure described in FIG. 7 using compounds with appropriate modification of compound 31. For example, compound 37 can be made from precursors to 31. Compound 37, after reacting with compound 30, yields compound 38 which, after several steps, yields compound 41. Compound 41, stirred in the presence of DBU, can undergo cyclization. After hydrolysis of the ester group, the acid 42 is formed (FIG. 8).

Figure 9:
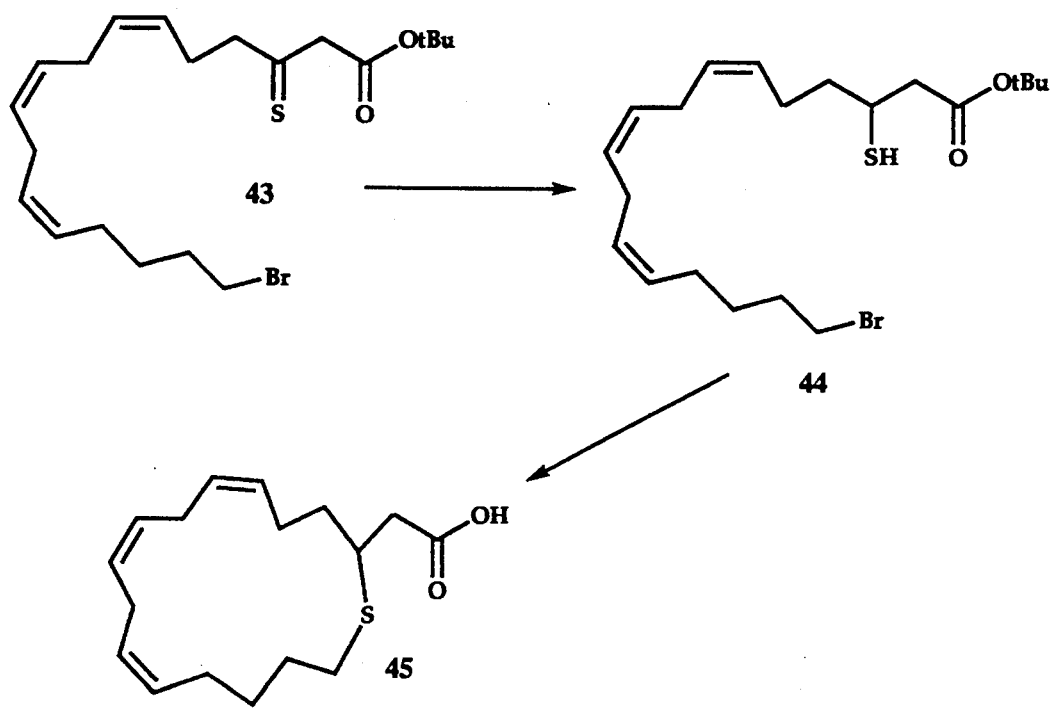
FIG. 9 is a schematic representation of the synthesis of compounds 44 and 45 of Example 1 from compound 43 of Example 1.
Figure 10:
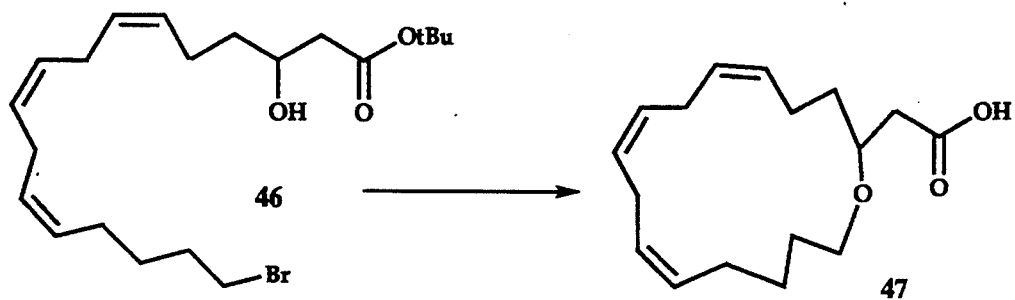
FIG. 10 is a schematic representation of the synthesis of compound 47 of Example 1 from compound 46 of Example 1.

The sulfur and oxygen-substituted ring compounds 45 and 47 can be made in an analogous fashion (FIGS. 9 and 10).

E. Synthesis of 17-Membered Hetero Atom-substituted Ring Linolenic Acid Analogs

Figure 8:
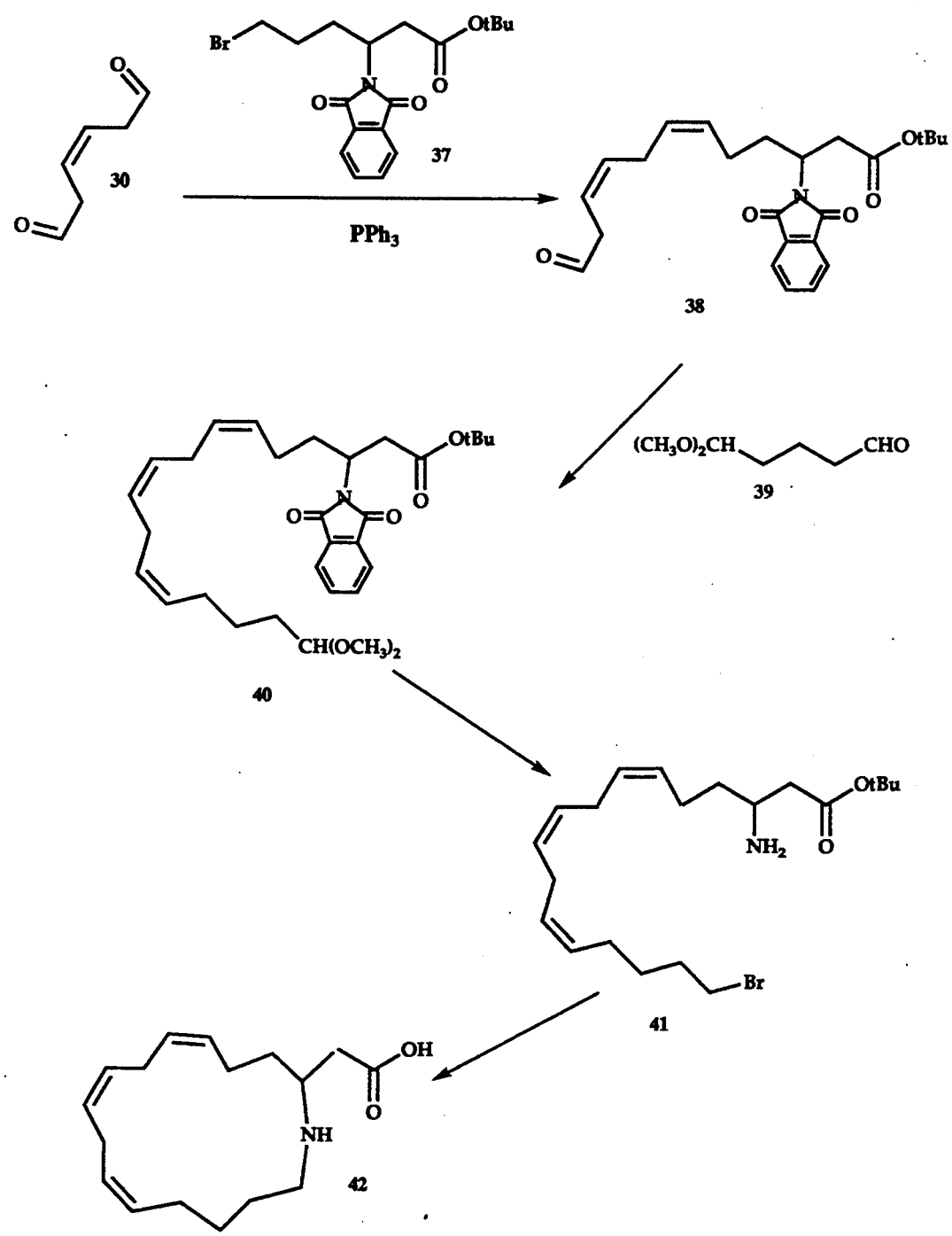
FIG. 8 is a schematic representation of the synthesis of compounds 38 and 40 to 42 of Example 1.
Figure 11:
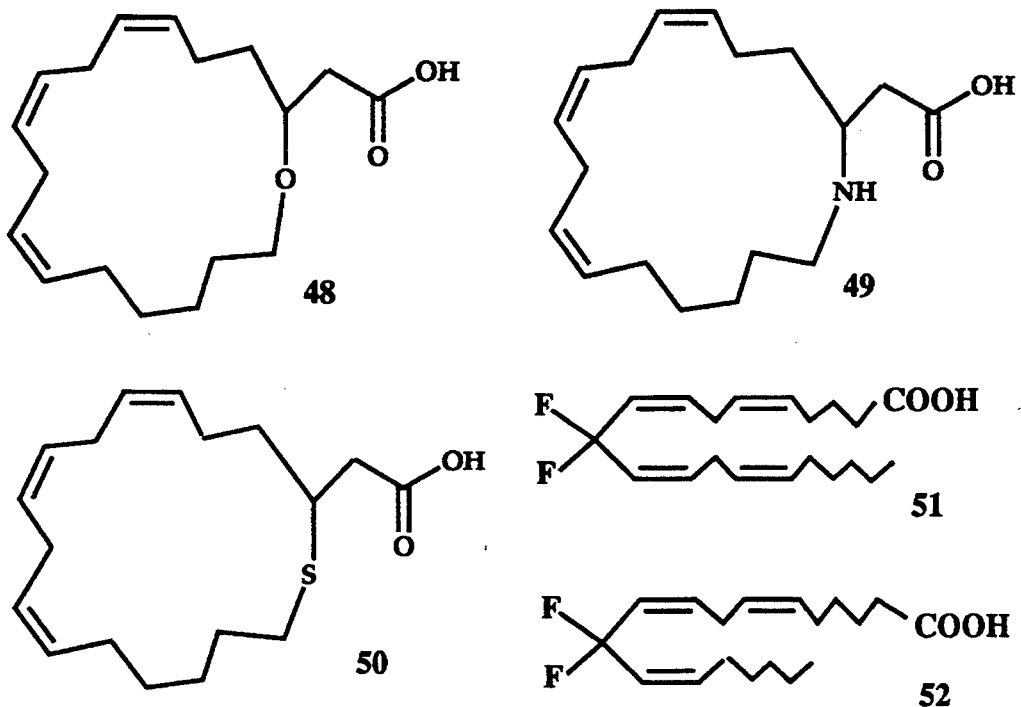
FIG. 11 shows the structures for compounds 48 to 50 of Example 1 which can be made using the scheme shown in FIG. 8.

Compounds 48, 49, and 50 (FIG. 11) can be made using the chemistry outlined in FIG. 8 by merely replacing the 5-carbon aldehyde 39 with its 6-carbon homologue 33.

F. Synthesis of polyunsaturated fatty acids with $CF_2$ group(s) in between cis double bonds A general methodology for the synthesis of unsaturated fatty acids, in which one of the methylene group between cis double bonds is replaced by a $CF_2$ group is available Kwok et al. J. Am. Chem. Soc. 109:3684 (1987)]. This is exemplified by the preparation of 10, 10-difluoroarachidonic acids (compound 51) and 11, 11-difluoro-γ-linoleic acid (compound 52 in FIG. 11).

G. Chemical names of compounds in FIGS. 1 to 11

1. Any acid.
2. The corresponding aldehyde.
3. Ethyl 3-hydroxyacid ester.
4. Ethyl 3-ketoacid ester.
5. Ethyl 3,3-difluoroacid ester.
6. 3,3-Difluoro acid.
7. Any acid chloride.
8. Meldrum's acid adduct.
9. 3-Keto acid.
10. 1,3-Cyclohexanedione.
11. Ethyl 6-bromohexanoate.
12. Ethyl 6-(2,6-cyclohexanedion-yl)hexanoate.
13. Ethyl 6-(2,6-dihydroxycyclo-hexanyl)hexanoate.
14. Ethyl 6-[2,6-bis(trifluoromethane sulfonyl)cyclohexanyl]heaxanoate.
15. Ethyl 6-(cyclohex-2,5-dienyl)hexanoate.
16. Cyclohexanone.
17. 2,6-Dibromocyclohexanone.

18. Ethyl 6-magnesiumbromo-hexanoate.
19. Ethyl 6-(1-hydroxy-2,6-dibromo-cyclohexyl)hexanoate.
20. Ethyl 6-(1-fluoro-2,6-dibromo-cyclohexyl)hexanoate.
21. Ethyl 6-(1-fluoro-cyclohex-2,5-dienyl)hexanoate.
22. Civetone.
23. Civetone trimethylsilyl-cyanohydrin.
24. 1-Hydroxycyclohept-9-ene-1-carboxylic acid.
25. Ethyl 1-hydroxycyclohept-9-ene-1-carboxylate.
26. Ethyl 1-fluorocyclohept-9-ene-1-carboxylate.
27. Ethyl 1-fluorocyclohept-9-ene-1-carboxylic acid.
28. Ethyl 1-fluoro-8,11-dibrocyclohept-9-ene-1-carboxylate.
29. Ethyl 1-fluorocyclohept-7,9,11-triene-1-carboxylic acid.
30. 3-Hexenedial.
31. Tert-butyl 6-bromo-3-ketohex-anoate resorcinol ketal.
32. Tert-butyl 3-keto-dodec-6,9-diene-12-carboxaldehydoate resorcinol ketal.
33. 6,6-Dimethoxyhexanal.
34. Tert-butyl 3-keto-18,18-dimethoxyoctadec-6,9,12-trienoate resorcinol ketal.
35. Tert-butyl 3-ketooctadeca-6,9,12-triene-18-carbox-aldehydoate.
36. 2-(1-Cyclohexadec-1,7,10,13-tetraenyl)acetic acid.
37. Tert-butyl 6-bromo-3-N-phthal-amidohexanoate.
38. Tert-butyl 3-N-phthalamido-dodec-6,9-diene-12-carbox-aldehydoate.
39. 5,5-Dimethoxypentanal.
40. Tert-butyl 3-N-phthalamido-18,18-dimethoxyoctadec-6,9,12-trienoate.
41. Tert-butyl 3-keto-18-bromo-octadeca-6,9,12-trienoate.
42. 2-(2-Azacyclohexadec-7,10,13-trienyl) acetic acid.
43. Tert-butyl 3-thio-18-bromo-octadeca-6,9,12-trienoate.
44. Tert-butyl 3-sulfhydryl-18-bromooctadeca-6,9,12-trienoate.
45. 2-(2-Thiacyclohexadec-7,10,13-trienyl)acetic acid.
46. Tert-butyl 3-hydroxy-18-bromo-octadeca-6,9,12-trienoate.
47. 2-(2-Oxacyclohexadec-7,10,13-trienyl) acetic acid.
48. 2-(2-Oxacycloheptadec-8,11,14-trienyl) acetic acid.
49. 2-(2-Azacycloheptadec-8,11,14-trienyl) acetic acid.
50. 2-(2-Thiacycloheptadec-8,11,14-trienyl) acetic acid.
51. 10,10-Difluoro-arachidonic acid.
52. 11,11-Difluoro-γ-linolenic acid.

EXAMPLE 2

Inhibition of 5α-Reductase Activity by Microsomal Lipids and Organic Solvent Extracts of Animal Organs and Plant Products In mammalian cells, 5α-reductase is very tightly associated with intracellular membranes, including the membrane of the endoplasmic reticulum and contiguous nuclear membranes. Attempts to solubilize and purify active 5α-reductase have not been very successful. The assay of 5α-reductase activity, therefore, has been performed by measuring the rate of conversion of testosterone to 5α-DHT by whole cells or by microsomal and nuclear preparations in the presence of NADPH (enzymatic assay). Alternatively, the 5α-reductase activity can be reliably assayed by following NADPH-dependent noncovalent binding of a potent radioactive inhibitor, such as [$^3$H]4-MA ([$^2$H]4-MA-binding assay), which strongly competes with testosterone for binding to the reductase. The results of the two assays correlate very well when microsomal preparations from different organs or animals are used for comparison [Liang et al., *Endocrinology* 112:1460 (1983)].

Figure 12:
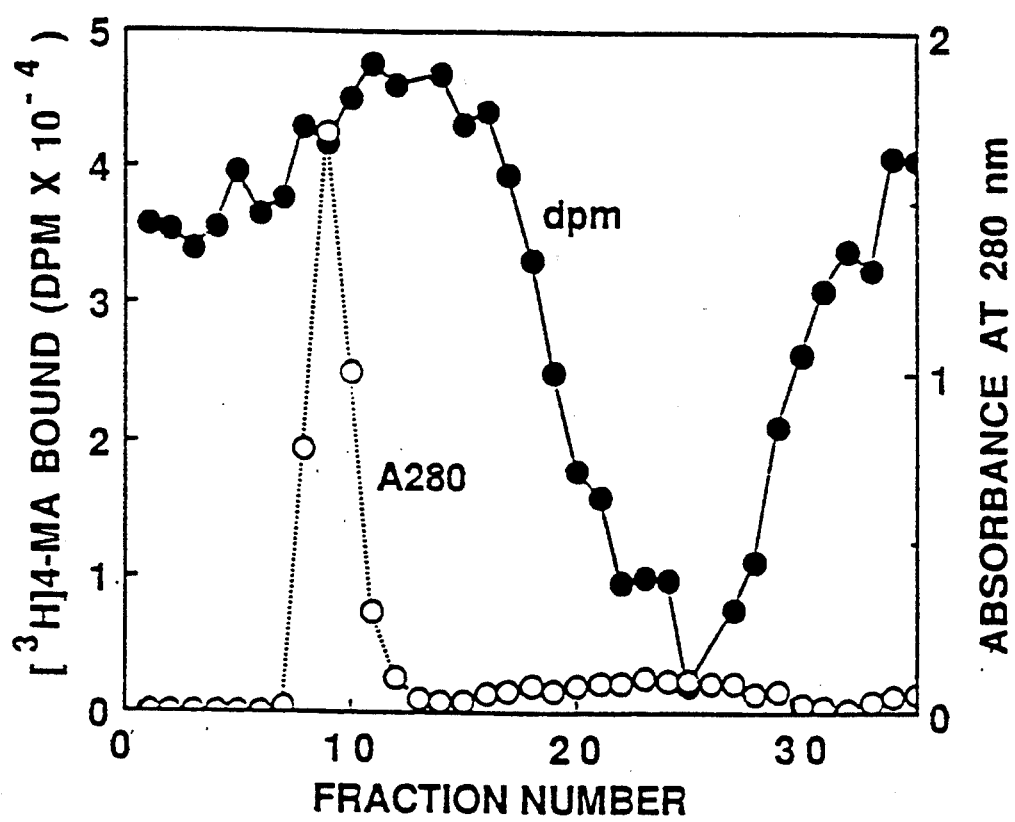
FIG. 12 shows the fractionation of 5α-reductase inhibitors in the microsomal extract of rat liver by Sephadex G-50 column chromatography. 5α-Reductase was assayed by the [$^3$H]4-MA-binding assay (closed circles). The absorbance at 280 nm for each fraction is also shown (open circles). Most of the inhibitory activity was associated with the fractions No. 19 to No. 29.

When the microsomal fraction of rat liver was solubilized with acetic acid and then mixed with methanol, more than 80% of microsomal proteins were removed as precipitates. This procedure inactivated the 5α-reductase activity completely. The soluble fraction, but not the precipitated fraction, contained compounds that inhibited 5α-reductase activity (determined by the enzymatic assay or [$^3$H]4-MA-binding assay) of rat liver microsomes. As shown in FIG. 12, Sephadex G-50 column chromatography of the methanol soluble fraction showed separation of the inhibitory activity from the majority of the protein peak which eluted in the void volume. The inhibitory activity was also found in methylene chloride extracts of rat liver microsomes, suggesting that some of the inhibitors were lipids. The inhibitory activity was also found in organic solvent extracts of beef liver, beef kidney, human placenta, rat and human prostates, yeast and plant (corn, peanut, olive, and other vegetable) oils, indicating that the inhibitors are present in various animal organs, plant products, and microorganisms.

EXAMPLE 3

Inhibition of 5α-Reductase Activity by Pure Lipids Using the [$^3$H]4-MA Binding Assay When various lipids were tested for their ability to affect binding of [$^3$H]4-MA to rat liver microsomes, only certain unsaturated fatty acids are inhibitory, as shown in Table 1. Among the lipids we have tested, the highly inhibitory fatty acids have 14 to 22 carbon chains and one to six double bonds. The presence of a double bond was required for higher inhibitory activity; saturated fatty acids were generally not as active as corresponding unsaturated fatty acids. With the [$^3$H]4-MA binding assay, only compounds with double bonds in the cis configuration were active at low concentrations (<10 μM), whereas the trans isomers were inactive even at high concentrations (>0.2 mM). However, as will be shown in Example 4, the trans isomers were active inhibitors when the reductase activity was analyzed using the enzyme assay. The difference in the effect of cis and trans isomers of fatty acids in the [$^3$H]4-MA binding assay is obvious when the following sets of fatty acids are compared: oleic acid (C18:1, cis-9) vs. elaidic acid (C18:1, trans-9) and linoleic acid (C18:2, cis-9,12) vs. linolelaidic acid (C18:2, trans-9,12). The results presented in Table 1 also demonstrate that the number and the position of the double bonds also affected the potency. When the [$^3$H]4-MA binding assay was used, the inhibitory potency for the C18 fatty acids were, in decreasing order: γ-linolenic acid (cis-6,9,12)>cis-6,9,12,15-octadecatetraenoic acid>α-linolenic acid (cis-9,12,15)>linoleic acid (cis-9,12)>oleic acid (cis-9)>petroselinic acid (cis-6). Erucidic acid (C22:1, cis-13) was inactive; whereas cis-4,7,10,13,16,19-docosahexaenoic acid was a potent inhibitor. Undecylenic acid (C11:1,10) and nervonic acid (C24:1, cis-15) were also inactive.

A free carboxyl group is important since the methyl ester and alcohol analogs of these inhibitory unsaturated fatty acids were either inactive or only slightly active. Prostaglandin E2, F2a and I2 were not active; whereas the prostaglandin A1, A2, B1, B2, D2, E1, and F1a were somewhat active at 0.2 mM. Carotenes, retinals, and retinoic acid were also inactive. Phosphatidylcholine, phosphatidyl ethanolamine, 3-diolein, retinol, 13-cis-retinoic acid, and 13-cis-retinol were slightly stimulatory.

α- and β-carotenes, retinoic acid, 9-cis-retinal, retinal, and 13-cis-retinal. At this high concentration, some aliphatic lipids showed inhibitory activities that were significantly lower than the corresponding unsaturated fatty acids (percent inhibition in the parentheses): mirystoleic acid methyl ester (27%), γ-linolenic acid methyl ester (32%), and cis-4,7,10,13,,16,19-docosahexaenol (51%). Retinol, 13-cis retinoic acid, and 13-cis-retinol showed 58% stimulation at 200 μM but no stimulation or inhibition at 40 μM. IC50 (the concentrations needed to show 50% inhibition) for potent fatty acids were: γ-linolenic acid (10 μM), octadecatetraenoic acid (57

TABLE 1

Inhibition of [$^3$H]4-MA binding to 5α-reductase of rat liver microsomes by lipids

| Test compounds | | % Inhibition of [$^3$H]4-MA binding* Concentration of test compounds | | |
|---|---|---|---|---|
| Name | Numeric symbol # | 10 μM | 40 μM | 200 μM |
| Control (no addition) | | | | |
| Undecylenic acid | C11:1 (10) | | NA | 13 ± 2 |
| Myristoleic acid | C14:1 (cis-9) | NA | 25 ± 4 | 43 ± 1 |
| Palmitic acid | C16:0 | NA | | |
| Palmitoleic acid | C16:1 (cis-9) | NA | 16 ± 5 | 73 ± 7 |
| Palmitoleic acid methyl ester | | | NA | NA |
| Palmitoleyl alcohol | | | NA | 16 ± 4 |
| Stearic acid | C18:0 | NA | NA | NA |
| Petroselinic acid | C18:1 (cis-6) | | NA | 52 ± 9 |
| Oleic acid | C18:1 (cis-9) | NA | 16 ± 6 | 63 ± 12 |
| Elaidic acid | C18:1 (trans-9) | NA | NA | NA |
| Oleic acid methyl ester | | | NA | NA |
| Oleyl alcohol | | | NA | NA |
| Linoleic acid | C18:2 (cis-9,12) | NA | 12 ± 3 | 86 ± 4 |
| Linolelaidic acid | C18:2 (trans-9,12) | | NA | 19 ± 5 |
| Linoleic acid methyl ester | | | NA | NA |
| Linoleyl alcohol | | NA | NA | 25 ± 5 |
| α-Linolenic acid | C18:3 (cis-9,12,15) | 19 ± 3 | 27 ± 7 | 84 ± 6 |
| α-Linolenic acid methyl ester | | NA | NA | NA |
| α-Linolenyl alcohol | | NA | NA | 24 ± 1 |
| γ-Linolenic acid | C18:3 (cis-6,9,12) | 50 ± 2 | 83 ± 12 | 96 ± 2 |
| Octadecatetraenoic acid | C18:4 (cis-6,9,12,15) | NA | 40 ± 6 | 88 ± 2 |
| Arachidonic acid | C:20:4 (cis-5,8,11,14) | NA | 30 ± 10 | 88 ± 5 |
| Docosahexaenoic acid | C:22:6 (cis-4,7,10,13,16,19) | NA | 27 ± 1 | 87 ± 6 |
| Erucic acid | C:22:1 (cis-13) | | NA | NA |
| Nervonic acid | C-24:1 (cis-15) | | NA | NA |

(Table 1 continued):
Lipids were tested at concentrations ranged from 0.01 to 0.2 mM. Each experiment was carried out in duplicates and several experiments were performed to assure that the results shown are representative. Compounds that showed less than 10% inhibition were considered not active (NA). At 200 μM, no significant effect was observed with (a) saturated aliphatic fatty acids including caproic acid, heptanoic acid, caprilic acid, nonanoic acid, capric acid, undecanoic acid, lauric acid, tridecanoic acid, myristic acid, pentadecanoic acid, nonadecanoic acid, arachidic acid, heneicosanoic acid, behenic acid, tricosanoic acid, and lignocenic acid, (b) fatty acyl esters and alcohols including stearic acid methyl ester, S-stearoyl coA, palmitic acid methyl ester, S-palmitoyl CoA, cis-9-tetradecenol, and arachidonyl alcohol, and (c) vitamin A related compounds including α- and β-carotenes, retinoic acid, 9-cis-retinal, retinal, and 13-cis-retinal. At this high concentration, some aliphatic lipids showed inhibitory activities that were significantly lower than the corresponding unsaturated fatty acids (percent inhibition in the parentheses): mirystoleic acid methyl ester (27%), γ-linolenic acid methyl ester (32%), and cis-4,7,10,13,,16,19- docosahexaenol (51%). Retinol, 13-cis retinoic acid, and 13-cis-retinol showed 58% stimulation at 200 μM but no stimulation or inhibition at 40 μM. IC50 (the concentrations needed to show 50% inhibition) for potent fatty acids were: γ-linolenic acid (10 μM), octadecatetraenoic acid (57 μM), γ-linolenic acid (60 μM), arachidonic acid (65 μM), palmitoleic acid (108 μM), linoleic acid (117 μM), and oleic acid (128 μM).
The numeric symbol indicates the numbers of carbon atoms and the double bond(s) in the molecule. The numbers in parentheses indicate the positions of double bonds (numbered from the carboxyl end) in cis or trans forms.

Lipids were tested at concentrations ranged from 0.01 to 0.2 mM. Each experiment was carried out in duplicates and several experiments were performed to assure that the results shown are representative. Compounds that showed less than 10% inhibition were considered not active (NA). At 200 μM, no significant effect was observed with (a) saturated aliphatic fatty acids including caproic acid, heptanoic acid, caprilic acid, nonanoic acid, capric acid, undecanoic acid, lauric acid, tridecanoic acid, myristic acid, pentadecanoic acid, nonadecanoic acid, arachidic acid, heneicosanoic acid, behenic acid, tricosanoic acid, and lignocenic acid, (b) fatty acyl esters and alcohols including stearic acid methyl ester, S-stearoyl coA, palmitic acid methyl ester, S-palmitoyl CoA, cis-9-tetradecenol, and arachidonyl alcohol, and (c) vitamin A related compounds including μM), γ-linolenic acid (60 μM), arachidonic acid (65 μM), palmitoleic acid (108 μM), linoleic acid (117 μM), and oleic acid (128 μM).

The numeric symbol indicates the numbers of carbon atoms and the double bond(s) in the molecule. The numbers in parentheses indicate the positions of double bonds (numbered from the carboxyl end) in cis or trans forms.

EXAMPLE 4

Inhibition of 5α-Reductase Activity by Pure Lipids Using the Enzyme Assay Method When the inhibitory effects of fatty acids were tested by the enzymatic assay, the relative potency of saturated and cis unsaturated fatty acids were in agreement with that obtained by the [³H]4-MA-binding assay (Table 1), regardless of whether rat liver microsomes or prostate microsomes were used as the source of the enzyme. The trans isomers, elaidic acid (C18:1, trans-9) and linolelaidic acid (C18:2, trans-9,12), however, were much less inhibitory than their cis isomers, oleic acid (C18:1, cis-9) and linoleic acid (C18:2, cis 9,12), in the [³H]4-MA binding assay (Table 1 and FIG. 13, left), but they were as potent as their cis isomers in the enzymatic assay using either prostate microsomes or liver microsomes (FIG. 13, right). Therefore, the trans isomers appear to inhibit 5α-reductase through a different mechanism.

EXAMPLE 5

Kinetic Studies of γ-Linolenic Acid Inhibition of 5α-Reductase

Figure 14:
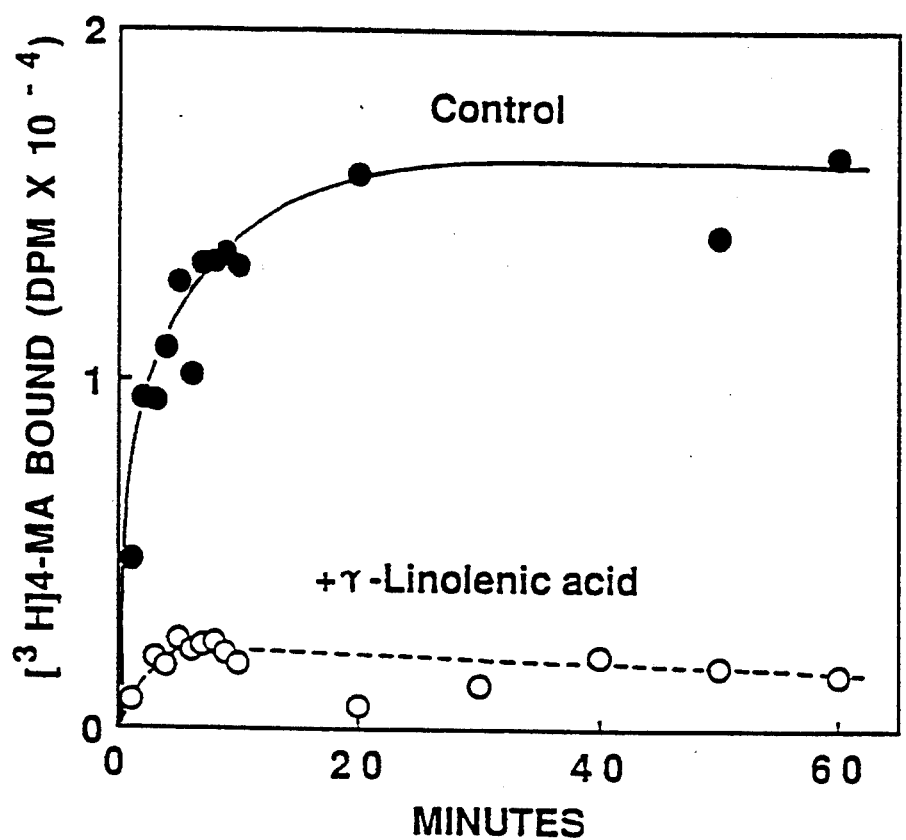
FIG. 14 shows the time course of γ-linolenic acid inhibition of [$^3$H]4-MA-binding to rat liver microsomes (5 μg protein). The concentration of γ-linolenic acid was 5 μM.
Figure 17:
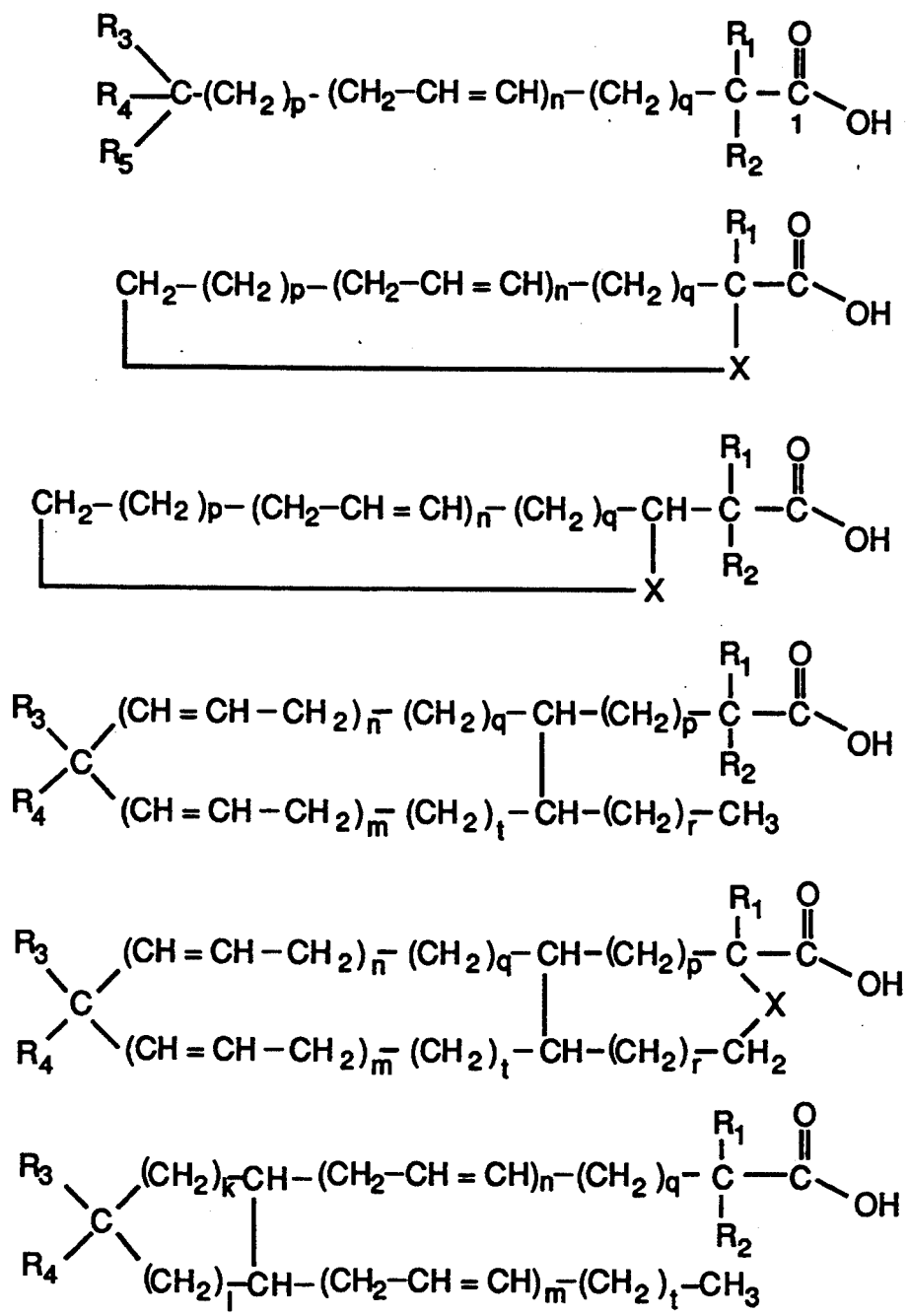
FIG. 17 shows a general formula for compounds that are part of the present disclosure. $R_1$, $R_2$, $R_3$, $R_4$, $R_5$, $R_6$, $R_7$, $R_8$, or $R_9$ may be a hydrogen, a fluorine or other halogen, or a methyl, ethyl, propyl, other alkyl or aryl group; one or two fluorine or other halogen atom(s) may replace hydrogen attached to any carbon atom(s) and 'l', 'm', 'n', 'p', 'q', 'r', and 't' are each independently 0 or an integer from 1 to about 50 and, preferably from 1 to about 30. The alkyl or aryl group and fluorine or other halogens attached to the molecules may protect them from degradation by oxidation of the unsaturated double bonds and α, β or ω oxidation. Oxidation products and metabolites of these fatty acids are also included since they are also expected to regulate 5α-reductase activity. Also —CH and the —OH groups can be in a substituted form (—CR and/or —OR) wherein —R represents an alkyl or an aryl group. Also included are acylates and esters that, upon hydrolysis, can form the carboxylic acid shown. 'X' can be a carbon, a sulfur, an oxygen, or a —NH—. This X—linkage is not limited to link carbon 2 and the carbon at the end of the chain; the link can be between any two carbons in the carbon chain.
Figure 19:
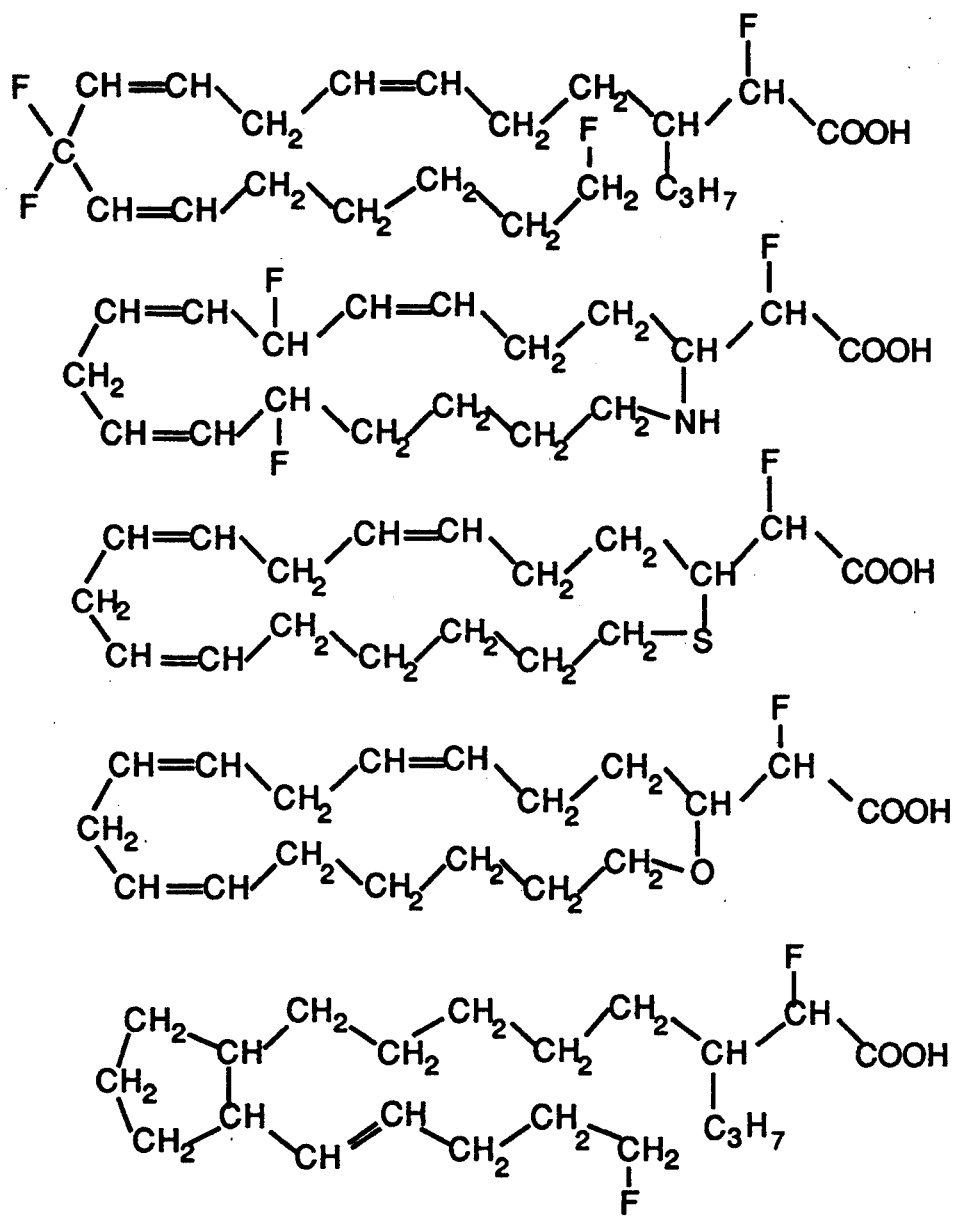
FIG. 19 shows examples of fluorinated and cyclic derivatives of fatty acids that are part of the present disclosure.

With either the enzymatic assay or with the [³H]4-MA binding assay (FIG. 14), inhibition was observed within a minute after γ-linolenic acid was mixed with the microsomal enzyme preparation and was observed with both intact and detergent (polyoxyethylene ether) solubilized rat liver microsomes (FIG. 15). As the concentrations of protein increased from 2 to 20 μg, the extent of inhibition by 10 μM γ-linolenic acid decreased from 93% to 52% for intact microsomes and from 96% to 88% for solubilized microsomes.

When [³H]4-MA was first allowed to bind to microsomes in the presence of NADPH, followed by addition of γ-linolenic acid to a final concentration of 10 μM, about 60% of the microsome-bound [³H]4-MA dissociated from the microsomes within 2 min. The remaining microsome-bound [³H]4-MA dissociated at a much slower rate over the next 60 min. To determine whether γ-linolenic acid inhibition is reversible, microsomes were incubated with γ-linolenic acid and then reisolated to remove free γ-linolenic acid. The results showed that the inhibition was only partially reversed (reduced from 78% to 63% inhibition). It is possible that γ-linolenic acid was bound tightly to microsomes and/or irreversibly inactivated components which were essential for the reductase activity.

By either the enzymatic or the [³H]4-MA binding assay, the inhibition could not be overcome by increasing the level of NADPH or testosterone (FIG. 16). γ-Linolenic acid did not appear to compete with testosterone or NADPH for their binding to the microsomal reductase. Double reciprocal plots of the data showed that 5 μM of γ-linolenic acid increased the apparent $K_m$ value for NADPH (from 2.0 to 3.1 μM) and testosterone (from 2.4 to 4.5 μM), and decreased the Vmax from 7.5 to 2.8 pmol 5α-DHT formed/mg protein/15 min. γ-Linolenic acid at 5 and 10 μM increased the apparent $K_i$ values for [³H]4-MA from 13 to 20 and 40 μM, respectively, and decreased the maximal binding from 0.56 to 0.45 and 0.40 pmol/10 μg protein, respectively.

EXAMPLE 6

Effect of γ-Linolenic Acid on other Microsomal Enzymes

The effect of γ-linolenic acid on the activities of another microsomal reductase and a microsomal enzyme that uses asteroid as a substrate was tested to determine the specificity of the effect of γ-linolenic acid. γ-Linolenic acid at 10 to 40 μM did not affect the activities of NADH:menadione reductase or UDP-glucuronic acid:5α-DHT glucuronosyl transferase.

Mammalian 5α-reductase is a cellular membrane-bound enzyme. Perturbation of the lipid matrix of the membranes may affect reductase activity nonspecifically. The fact that only unsaturated fatty acids with specific configurations were potent inhibitors of 5α-reductase in a specific assay and that two other microsomal enzymes examined are not affected suggests that the inhibition was selective.

EXAMPLE 7

Inhibition of the 5α-Reductase Activities of Human Liver Microsomes and Human Prostate Cancer Cells by γ-Linolenic Acid γ-Linolenic acid also inhibited NADPH-dependent [³H]4-MA binding to human liver microsomes to the same degree as in experiments with rat liver microsomes. The 5α-reduction of [³H]testosterone by human prostate cancer cells in culture was also selectively affected by Γ-linolenic acid. Table 2 shows that γ-linolenic acid, at 5 to 50 μM, inhibited 5α-reduction of [³H]testosterone in both the androgen-sensitive LNCaP cells [Horszewicz et at., Cancer Res. 43:1809 (1983)] and the androgen insensitive PC-3 cells [Kaighn et at., Invest. Urol. 17:16 (1979)]. γ-Linolenic acid, however, did not affect the metabolism of testosterone to 4-androstenedione, suggesting that 17 β-steroid dehydrogenase was not sensitive to the unsaturated fatty acid. Stearic acid (5 to 20 μM) did not affect the 5α-reductase or 17 γ-steroid dehydrogenase of PC-3 cells in culture.

The fact that specific 5α-reductase inhibition was observed with intact prostate cells in culture indicates that externally added fatty acids were able to enter cells and exert their inhibitory action on the endoplasmic reticulum or nuclear membrane-bound 5α-reductase in situ. It is, therefore, expected that the compounds of the present invention can be used as external agents, for example topically applied ointments or creams to control the overactive androgen actions in diseased organs.

TABLE 2

Inhibition of the formation of radioactive 4-androstenedione and 5α-DHT from [³H]testosterone by human prostatic cancer cells in culture by γ-linolenic acid

| Prostate cell line | Fatty acid added μM | Metabolites formed* 4-Androstendione % of control | 5α-DHT % of control |
|---|---|---|---|
| PC-3 | None (control) | 100 | 100 |
|  | γ-Linolenic acid |  |  |
|  | 1 | 102 ± 6 | 98 ± 6 |
|  | 5 | 110 ± 1 | 50 ± 3 |
|  | 20 | 99 ± 2 | 2 ± 2 |
|  | Stearic acid |  |  |
|  | 5 | 103 ± 2 | 123 ± 2 |
|  | 20 | 106 ± 5 | 121 ± 5 |
| LNCaP | None (control) | ND | 100 |
|  | γ-Linolenic acid |  |  |
|  | 50 | ND | 27 ± 0 |
|  | 100 | ND | 9 ± 4 |

(Table 2 continued):
*The control values for the formation of 4-androstenedione and 5α-DHT by PC-3 cells were 400,851 ± 9,507 dpm and 12,183 ± 74 dpm respectively. The control value for the formation of 5α-DHT by LNCaP was 4,569 ± 505 dpm. No 4-androstenedione formation was detected when LNCaP was used.

γ-Linolenic acid and stearic acid, at the concentrations tested, did not produce any visible change in cell morphology during the 2 hour incubation. $IC_{50}$ values (four experiments) for γ-linolenic acid with the prostate cancer cells were 10 ± 5 μM.

EXAMPLE 8

Other Lipids that Generate Fatty Acids and Phospholipids

Many of the potent unsaturated fatty acids are natural components of mammalian lipids. The acylated unsaturated fatty acids constitute about 50% of total fatty acid in mammalian triglycerides and phospholipids. Although these conjugated acids are not inhibitory in the cell-free assays, free acids can be generated from these lipids by lipases in the cells [Lands, Ann. Rev. Biochem. 34:313 (1965)] and inhibit 5α-reductase. Since DHT stimulates sebum production and promotes acne, it is worth noting that lipids from the scalp of patients with severe acne have been found to contain less linoleic acid than that of normal subjects [Morello et at., Invest. Derm. 66:319 (1976)]. Administration of fatty acids that can inhibit 5α-reductase is expected to reverse the pathogenic situation.

The stimulatory effect of certain phospholipids on 5α-reductase activity has been reported previously [Ichihara and Tanaka, Biochem. Biophys. Res. Comm. 149:482 (1981); Cooke and Robaire, J. Biol. Chem. 260:7489 (1985)]. The inventors also found that L-α-phosphatidylcholine and L-α-phosphatidyl-ethanolamine can stimulate 5α-reductase. Phospholipids may affect the conformation of 5α-reductase. Whether unsaturated fatty acids can counteract the phospholipid stimulation is not known. Retinoic acid had been previously reported to inhibit 5α-reductase in the human prostate cancer cell PC-3 and in PC-3 cell homogenates [Halgunset et at., J. Steroid Biochem. 28:731 (1983)]; inhibition was shown to be competitive with NADPH. The inventors, however, found that retinoic acid at 40 to 200 μM had no effect on 5α-reductase activity when the rat liver microsomal reductase was assayed.

EXAMPLE 9

Mechanism of Inhibition of 5α-Reductase by Fatty Acids

The ability of γ-linolenic acid to inhibit 5α-reductase in solubilized microsomes suggests that the }-linolenic acid inhibition may not be rigidly dependent on the native structure of endoplasmic reticulum membranes. Whether the fatty acid inhibitors act by interacting with the reductase and/or other components that are vital for reductase activity is not clear. The inhibitory fatty acids may also interact with and potentiate other endogenous inhibitors or lipids.

The proposed mechanism [Brantit et al., J. Steroid Biochem. Mol. Biol. 37:575 (1990)] of 5α-reductase (E) reaction includes the following steps:

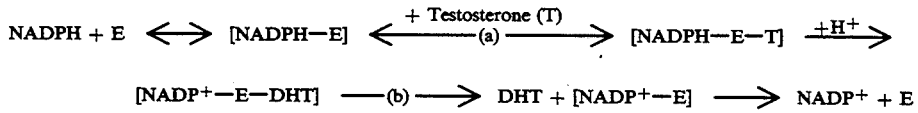

It is intriguing that two trans isomers of fatty acids tested, elaidic acid and linolelaidic acid, did not have any significant inhibitory activity in the [³H]4-MA binding assay but they were as potent as their cis isomers, oleic acid and linoleic acid, in the enzymatic assay. It is possible that the cis unsaturated fatty acids inhibit the formation of [NADPH-E-T] (step a); whereas the trans isomers act on steps after the formation of the ternary complex (step b). Steroidal inhibitors that can inhibit either step a or step b have been found [Liang and Heiss, J. Biol. Chem. 256:7998 (1981); Liang et al., Endocrinology 115: 2311(1984); Liang et al., J. Biol. Chem. 260:4890 (1985); Brandt et al., J. Steroid Biochem. Mol. Biol. 37:575 (1990)].

EXAMPLE 10

Effects of Polyunsaturated Fatty Acids and Other Compounds on Androgen Action in Animals, with Special Reference to Hamster Flank Organ Model Androgenic and antiandrogenic activities of various compounds in animals can be estimated by administration of these compounds to androgen deficient animals and measurement of the effect of these compounds on the growth of male accessory reproductive organs (e.g., prostate, seminal vesicles, or chick combs) [Liao and Fang, Vitamins and Hormones 27:17 (1969)]. Another organ which is especially useful in the evaluation of the effects of these compounds on skin cells or sebaceous glands is the hamster flank organ [Frost and Gomez, Adv. Biol. Skin. 12:403 (1972)]. The flank organs are composed of sebaceous glands and are androgen responsive tissues. Those typically studied are from the back of the golden hamster.

Tests are performed using normal or castrated hamsters. The test compounds (γ-linolenic acid or other test compounds at different concentrations) alone or in combination with an androgen are applied to hamsters fed with a complete diet or a diet deficient in essential fatty acids.

In mature male hamsters the flank organs are darker and larger than those of females or immature males. Castration of adult males causes regression of these glands while androgen administration stimulates their growth. Test compounds may be applied topically to only one of the two organs. Comparisons between the responses of the treated and the untreated organs on the same animal allow determination of whether the compound is topically active only, or it also has systemic effects.

EXAMPLE 11

Topical Effects of Polyunsaturated Fatty Acids and Other Compounds on Hair Loss and Growth in Stamptailed Macaque Monkeys The Stamptail macaque monkey develops baldness in a pattern resembling human adrogenetic alopecia. The balding process begins shortly after puberty (approximately 4 years of age). This occurs in nearly 100% of the animals, males and females, and is androgen dependent. This is a useful animal model for human androgenetic alopecia.

Male stamptailed macaques (4 years of age) are divided into groups of 3 to 5 animals. A defined area of the scalp involving the frontal and vertex areas is marked, e.g. by tatoo. Hairs in the marked area are shaved. The solutions of a testing compound in different dosages and combinations are evenly applied to the shaved areas once or twice a day. Control animals receive the same volume of the solvent (e.g., ethanol or other organic solvent, or a cream). The same area of the scalp is shaved every 4 to 6 weeks and the weights of hairs shaved are determined. The treatments may last for 6 months to 2 years. 4-MA (17-N,N-diethylcarbamoyl-4-methyl4-aza-5-androstan-3-one), a 5α-reductase inhibitor known to prevent baldness in this animal is included as a positive control.

Biopsies of the scalp (4 mm punch) are obtained before and at the end of the treatments. The specimens are analyzed for 5α-reductase activity and examined histologically for evidence of alopecia.

EXAMPLE 12

Topical Effects of Polyunsaturated Fatty Acids and Other Compounds on Rat Skin

Another useful animal model for skin is the rat model. In rat sebaceous glands, as in human (but not in the hamster flank organ model), sebum lipids are synthesized in the intermediate cells by the smooth endoplasmic reticulum (SER). The volume density of SER, as seen under electron microscopic examination, depends on androgen [Moguilewsky and Bouton, *J. Steroid Biochem.* 31:699 (1988)]. Since repression of androgen action can cause reduction of this density, the effectiveness of test compounds, systemically or topically administered to rats, can be evaluated by measuring their ability to reduce the volume density of SER.

EXAMPLE 13

Topical Effects of Polyunsaturated Fatty Acids and Other Compounds on Hirsutism and Skin Diseases Such As Hyperseborrhea and Acne The topical antiandrogenic activity of a test compound can be evaluated by the hamster flank organ assay or the rat assay. However, the effectiveness of a compounds must be tested in humans since animal models may not always mimic the situation in man [Moguilewsky and Bouton, *J. Steroid Biochem.*31:699 (1988)]. The ideal compounds for human treatment are those that are topically and locally active but do not show systemic antiandrogenic activity, especially in the cases involving young males. The effect of the test compounds can be analyzed by measuring sebum secretion from the foreheads of volunteers or patients treated topically with the test compound.

EXAMPLE 14

Methods for Delivery and Application of Polyunsaturated Fatty Acids As Antiandrogenic Compounds Polyunsaturated fatty acids can be used as antiandrogenic agents through topical or systemic application. A preparation for this purpose can include a carrier, a protectant, an antioxidant (such as vitamin C or E), and other pharmaceutical and pharmacological agents. It is also expected that such fatty acids can be used in a delivery system involving molecular recognition through which the said fatty acids are delivered to target sites. Such a delivery system may involve, among other methods, liposome techniques or immunological devices.

What is claimed is:

1. A method of selectively inhibiting 5α-reductase in an intact cell, comprising contacting said cell with a $C_{14}$–$C_{22}$ unsaturated aliphatic fatty acid or alcohol in an amount sufficient to prevent reduction of androgen by the 5α-reductase.

2. The method of claim 1 wherein the unsaturated fatty acid has 1–6 double bonds.

3. The method of claim 2 wherein the unsaturated double bonds are in the cis configuration.

4. The method of claim 2 wherein the unsaturated double bonds are in the trans configuration.

5. The method of claim 1 wherein the fatty acid is selected from the group consisting essentially of docosahexaenoic acid, arachidonic acid, octadecatetraenoic acid, γ-linolenic acid α-linolenic acid, linolelaidic acid, linoleic acid, elaidic acid, oleic acid, petroselinic acid palmitoleic acid myristoleic acid and undecylenic acid.

6. The method of claim 1 wherein the fatty alcohol is selected from a group consisting essentially of palmitoleyl alcohol, linoleyl alcohol, and α-linolenyl alcohol.

7. The method of claim 4 wherein the fatty acid is γ-linolenic acid.

8. The method of claim 1 wherein the fatty acid is octadecatetraenoic acid.

9. The method of claim 1 wherein the fatty acid is arachidonic acid.

10. The method of claim 1 wherein the fatty acid is docosahexaenoic acid.

11. The method of claim 1 wherein the fatty acid is α-linolenic acid or linoleic acid, 12. The method of claim 1 wherein the cell is a liver, a skin or a prostate cell.

13. The method of claim 1 wherein the androgen is testosterone.

14. A method of inhibiting 5α-reductase activity comprising measuring the rate of conversion of testosterone to 5α-DHT in the presence of a compound of claim 5 or claim 6 wherein lower conversion rates in the presence of the compound are indicative of 5α-reductase inhibition.

15. The method of claim 14 wherein the compound is γ-linolenic acid.

16. The method of claim 14 wherein the compound is elaidic acid or linolelaidic acid.

17. A method of treating a mammal having a condition responsive to control of testerone levels, comprising administering topically or systemically a pharmaceutical composition of a fatty acid of claim 1.

18. The method of claim 17 wherein the condition is excessive growth of an androgen responsive organ or tissue.

19. The method of claim 17 wherein the condition is excessive pigmentation.

* * * * *

UNITED STATES PATENT AND TRADEMARK OFFICE
CERTIFICATE OF CORRECTION

PATENT NO. : 5,422,371
DATED : Kime 6, 1995
INVENTOR(S) : Shutsung Liao, et. al.

It is certified that error appears in the above-identified patent and that said Letters Patent is hereby corrected as shown below:

In column 1, line 5, before "CROSS-REFERENCED AND RELATED" insert --The government owns rights in the present invention pursuant to grant/contract number DK41670 from the National Institute of Health.--.

Title page, item 57, line 11, please delete "disclose" and substitute -- disclosed -- therefor.

Signed and Sealed this

Twenty-second Day of August, 1995

Attest:

BRUCE LEHMAN

Attesting Officer

Commissioner of Patents and Trademarks